(12) United States Patent
Gao et al.

(10) Patent No.: US 11,667,857 B2
(45) Date of Patent: Jun. 6, 2023

(54) USE OF FERMENTATION TAIL GAS IN INTEGRATED GASIFICATION AND GAS FERMENTATION SYSTEM

(71) Applicant: LanzaTech, Inc., Skokie, IL (US)

(72) Inventors: Allan Haiming Gao, Skokie, IL (US); Robert John Conrado, Skokie, IL (US); Richard Rosin, Skokie, IL (US); Gregory Morin, Skokie, IL (US); Franz-Marcus Nowak, Skokie, IL (US)

(73) Assignee: LanzaTech, Inc., Skokie, IL (US)

( * ) Notice: Subject to any disclaimer, the term of this patent is extended or adjusted under 35 U.S.C. 154(b) by 91 days.

(21) Appl. No.: 17/180,583

(22) Filed: Feb. 19, 2021

(65) Prior Publication Data

US 2021/0284925 A1 Sep. 16, 2021

Related U.S. Application Data

(60) Provisional application No. 62/990,216, filed on Mar. 16, 2020.

(51) Int. Cl.
*B01D 53/02* (2006.01)
*B01D 53/96* (2006.01)
(Continued)

(52) U.S. Cl.
CPC .............. *C10J 3/84* (2013.01); *B01D 53/02* (2013.01); *B01D 53/96* (2013.01); *C10K 1/04* (2013.01);
(Continued)

(58) Field of Classification Search
CPC ........ C10J 2300/0916; C10J 2300/1681; C10J 2300/0946; C10J 2300/0923;
(Continued)

(56) References Cited

U.S. PATENT DOCUMENTS

2011/0138684 A1 6/2011 Kranz
2015/0152441 A1 6/2015 Schultz et al.
(Continued)

FOREIGN PATENT DOCUMENTS

JP          2018179528    * 10/2019  ........... B01D 53/047
WO     WO-2020067177 A1 *  4/2020  ........... B01D 53/047

OTHER PUBLICATIONS

International Search Report and Written Opinion issued in corresponding International Application No. PCT/US2021/020801, dated Jun. 24, 2021, 11 pages.

(Continued)

*Primary Examiner* — Imran Akram
(74) *Attorney, Agent, or Firm* — Maryann Maas

(57) ABSTRACT

The disclosure provides for the separation and combustion of at least one hydrocarbon, oxygenate, sulfur compound, and or nitrogen compound, from industrial gas or gasification derived syngas to generate steam. A gasification process and a gas fermentation process may be integrated using tail gas from the fermentation process for the flame to combust tar and other compounds from the syngas generated by a gasification process. Integration may be achieved by removing tar and other compounds from industrial gas or gasification derived syngas using an adsorbent and regenerating the adsorbent using tail gas from the gas fermentation process. Tail gas enriched with the desorbed tar and other compounds may be used to generate steam in a steam boiler and the steam may be used for a variety of purposes including power generation to power, for example, a compressor of the gas fermentation process.

10 Claims, 6 Drawing Sheets

(51) Int. Cl.
   *C12M 1/107*  (2006.01)
   *C10K 1/04*   (2006.01)
   *C10K 1/20*   (2006.01)
   *C10J 3/84*   (2006.01)

(52) U.S. Cl.
   CPC ........... *C10K 1/20* (2013.01); *C12M 21/04* (2013.01); *C10J 2300/1606* (2013.01); *C10J 2300/1643* (2013.01); *C10J 2300/1681* (2013.01); *C10J 2300/1687* (2013.01)

(58) Field of Classification Search
   CPC ....... Y02P 20/145; Y02P 20/59; C12M 21/04; C12M 21/12; C12M 43/00; C12P 7/065; C02F 11/04; B01D 53/84; B01D 53/96
   See application file for complete search history.

(56) References Cited

U.S. PATENT DOCUMENTS

| | | |
|---|---|---|
| 2015/0225749 A1 | 8/2015 | Hickey |
| 2018/0141000 A1 | 5/2018 | Winter et al. |
| 2019/0111378 A1* | 4/2019 | Ishii .................. B01D 53/8671 |
| 2019/0136138 A1* | 5/2019 | Feugnet ................. C10B 53/02 |
| 2022/0040673 A1* | 2/2022 | Natsuyama ............. B01J 20/18 |

OTHER PUBLICATIONS

Drake, Acetogenic Prokaryotes, In: The Prokaryotes, 3rd edition, p. 354, New York, NY, 2006.
Ragsdale, Biochim Biophys Acta, 1784: 1873-1898, 2008.

\* cited by examiner

USE OF FERMENTATION TAIL GAS IN INTEGRATED GASIFICATION AND GAS FERMENTATION SYSTEM

CROSS REFERENCE TO RELATED APPLICATIONS

This application claims the benefit of U.S. Provisional Patent Application No. 62/990,216 filed Mar. 16, 2020, the entirety of which is incorporated herein by reference.

FIELD OF THE INVENTION

The invention relates to processes for improving the integration of a gasification process and a gas fermentation process. In particular, the invention relates to employing at least a portion of the tail gas of the gas fermentation process to desorb at least one tar from an adsorbent used to separate tar from syngas produced by a gasification process before the syngas is used as a feed to the gas fermentation process. In another embodiment, the tail gas is used to regenerate adsorbent used to separate tar from industrial gas before the industrial gas is introduced to a gas fermentation process.

BACKGROUND

As the world population increases, the waste generated by such a population becomes a growing concern. One solution for waste disposal is gasification. Gasification is a process that converts organic or fossil fuel-based carbonaceous materials into syngas comprising carbon monoxide, carbon dioxide, and hydrogen. Gasification advantageously both reduces the amount of waste that ends up in a landfill and produces a product, syngas, which can be converted by one or more subsequent process to useful products.

Syngas produced by gasification may be utilized by a number of processes including Fischer-Tropsch. The Fischer-Tropsch process provides for the catalytic hydrogenation of carbon monoxide to produce a variety of products including hydrocarbons, alcohols, or other oxygenated hydrocarbons. However, the catalytic beds within the Fischer-Tropsch process are particularly sensitive to various components which may be in the syngas stream depending on the gasification feedstock. One such component is sulfur. If sulfur is not removed from the syngas stream prior to being sent to the Fischer-Tropsch process, the sulfur can deactivate the catalysts required for the Fischer-Tropsch reaction. Thus, in order to arrive at a suitable gas for the Fischer-Tropsch process, extensive gas clean-up technology is often required.

One alternative to the Fischer-Tropsch process is gas fermentation. Gas fermentation provides for the biological fixation of gases, including syngas, into one or more product. Gas fermentation has a variety of advantages over the Fischer-Tropsch process. Firstly, Fischer-Tropsch utilizes high temperatures (150-350° C.), elevated pressures (30 bar), and heterogeneous catalysts such as cobalt, ruthenium, and iron. In comparison, gas fermentation takes places at about 37° C. and is often conducted at atmospheric pressure, which presents significant energy and cost savings relative to the Fischer-Tropsch process. Additionally, the Fischer-Tropsch process requires a relatively fixed $H_2:CO$ ratio in the syngas, around 2:1, whereas gas fermentation is capable of receiving and utilizing a diverse range of substrates with varying $H_2:CO$ ratios.

Gasification converts biomass or municipal waste through partial oxidization into a gaseous mixture of syngas comprising carbon monoxide, hydrogen, methane, nitrogen, water vapor, carbon dioxide, and tars. Biomass derived syngas in particular, contains high concentrations of tarry compounds and particles which should be removed from the syngas is utilized. The tars often comprise a range of hydrocarbons and oxygenated. Examples include aromatics, polyaromatics, furanic backbone structures, with aliphatic and oxygenated functional groups such as acids, aldehydes, ketones, and alcohols, attached to the backbone. It is envisioned that industrial gas may also contain tars depending upon the source of the industrial gas.

There remains a need to efficiently remove tars from industrial gas or gasification derived syngas before the industrial gas or syngas may be utilized in a downstream process. In addition, there remains a need for a higher level of integration between a gasification operation and gas fermentation operation so that a waste stream of one operation is used in the most beneficial way for the overall system. An unexpectedly beneficial use of the tail gas from the gas fermentation operation is to employ at least a portion of the tail gas to regenerate adsorbent used to separate at least one tar from the syngas before the syngas is used as a feed to the gas fermentation operation. The degree of integration may be further increased by combusting the tail gas after desorption of the tar, and therefore enriched in tar and of higher calorific value, in a steam boiler to generate steam. There is a surprising quantity of residual energy in the tail gas enriched in tar and thus a surprising quantity of steam produced. Integration may be still further integrated by utilizing the steam to generate power for a compressor used in the gas fermentation operation. Other options include power generation such as in a gas engine or gas turbine.

BRIEF SUMMARY

The disclosure involves a method comprising treating a syngas stream from a gasification process or an industrial gas by adsorbing on an adsorbent at least one hydrocarbon and or oxygenate and generating a treated stream; fermenting at least a portion the treated stream in a bioreactor using a microorganism to generate an effluent comprising at least one product and a tail gas stream; regenerating the adsorbent by desorbing the at least one hydrocarbon or oxygenate using at least a portion of the tail gas stream to provide an enriched tail gas stream further comprising the desorbed at least one hydrocarbon or oxygenate; and utilizing at least a portion of the enriched the tail gas in at least one of the following: combusting in a steam boiler to produce steam; generating power; or recycling to a gasification process.

The disclosure further involves an apparatus comprising: an adsorption unit housing an adsorbent; a gasifier in fluid communication with the adsorption unit; a bioreactor in fluid communication with the adsorption unit; a tail gas conduit in fluid communication with the bioreactor and the adsorption unit; a steam generation unit; and an enriched tail gas conduit in fluid communication with the adsorption unit and the steam generation unit. The apparatus may further comprising a steam conduit in fluid communication with a power generation system. The apparatus may further comprising a compressor in electrical communication with the power generation system and in fluid communication with the bioreactor.

In one embodiment, the fermentation process utilizes one or more C1-fixing microorganisms, suitable to ferment C1-containing gaseous substrate, such as syngas produced through gasification. In various embodiments, the C1-fixing microorganism is selected from the group consisting of

*Moorella, Clostridium, Ruminococcus, Acetobacterium, Eubacterium, Butyribacterium, Oxobacter, Methanosarcina,* and *Desulfotomaculum*. The microorganism may be a member of the genus *Clostridium*. In certain instances, the microorganism is *Clostridium autoethanogenum*.

In various embodiments, the gasification feedstock is municipal solid waste, agricultural waste, microbial biomass, or any combination thereof. The gasification feedstock is dried in a drier and then gasified to produce a syngas stream. At least a portion of the syngas stream is passed to the fermentation process to produce one or more product and possibly at least one by-product. In some embodiments, the microbial biomass generated from the fermentation process is passed to the gasification operation as feedstock to the gasification.

In some embodiments, substantially all of the microbial biomass produced by the fermentation process is either recycled to the fermentation process following product recovery, treated by the wastewater treatment process and/or sent to the gasification process to produce syngas. In certain instances, the gasification process receives at least 20%, at least 30%, at least 40%, at least 50%, at least 60%, at least 70%, at least 80%, at least 90%, or substantially all of the microbial biomass from the fermentation process.

In some embodiments, the microbial biomass generated from the wastewater treatment process is sent to the gasification process. The microbial biomass generated from the wastewater treatment process may, at least in part, be recovered from the anaerobic digester process within the wastewater treatment process. In various instances, at least a portion of the microbial biomass from the wastewater treatment process is dried prior to being passed to the gasification process. In certain instances, substantially all of the microbial biomass from the wastewater treatment process is dried prior to being passed to the gasification process.

In particular embodiments, at least a portion of the microbial biomass depleted water from the fermentation process is sent to the gasification process. In various instances, the microbial biomass depleted water is sent to the gasification process to increase the $H_2$:CO ratio in the syngas stream. Preferably, at least a portion of the microbial biomass depleted water is sent to the gasification process to increase the $H_2$:CO ratio in the syngas stream to at least 2:1, at least 3:1, or at least 4:1. Sending the microbial biomass depleted water to the gasification process, where the $H_2$:CO ratio in the syngas stream is increased, may result in increased selectivity to ethanol produced by the gas fermentation process, decreased selectivity to microbial biomass production, decreased water consumption by the fermentation reaction, and/or a reduced bleed flow to the wastewater treatment process.

In particular embodiments, at least a portion of wastewater generated from the fermentation process is sent to the gasification process. This wastewater may contain one or more product and/or by-product including but not limited to microbial biomass. In various instances, the wastewater generated from the fermentation process is sent to the gasification process to increase the $H_2$:CO ratio in the syngas stream. Preferably, at least a portion of the wastewater generated from the fermentation process is sent to the gasification process to increase the $H_2$:CO ratio in the syngas stream to at least 2:1, at least 3:1, or at least 4:1. Sending the wastewater generated from the fermentation process to the gasification process, where the $H_2$:CO ratio in the syngas stream is increased, may result in increased selectivity to ethanol produced by the gas fermentation process, decreased selectivity to microbial biomass production, decreased water consumption by the fermentation reaction, and/or a reduced bleed flow to the wastewater treatment process.

In particular embodiments, at least a portion of the clarified water from the wastewater treatment process is sent to the gasification process. In various instances, the clarified water from the wastewater treatment process is sent to the gasification process to increase the $H_2$:CO ratio in the syngas stream. Preferably, at least a portion of the clarified water from the wastewater treatment process is sent to the gasification process to increase the $H_2$:CO ratio in the syngas stream to at least 2:1, at least 3:1, or at least 4:1. Sending the clarified water from the wastewater treatment process to the gasification process, where the $H_2$:CO ratio in the syngas stream is increased, may result in increased selectivity to ethanol produced by the gas fermentation process, decreased selectivity to microbial biomass production, decreased water consumption by the fermentation reaction, and/or a reduced bleed flow to the wastewater treatment process.

Preferably, at least a portion of at least one effluent from the fermentation process and/or the wastewater treatment process replaces at least a portion of the process water required by the gasification process. In certain instances, the process water required by the gasification process is reduced by at least 45 percent. In at least one embodiment, the process water required by the gasification process is reduced between 45 to 100 percent. In certain embodiments, the process water required by the gasification process is reduced between 45 and 75 percent, 55 to 75 percent, 65 to 75 percent, 55 to 100 percent, 65 to 100 percent, or 75 to 100 percent.

In certain instances, at least a portion of at least one effluent is injected into the syngas stream produced by the gasification process to reduce the temperature of the syngas stream. Preferably, the effluent injected into the syngas stream produced by the gasification process is selected from the group consisting of: microbial biomass depleted water, wastewater generated from the fermentation process, and clarified water from the wastewater treatment plant. Preferably the temperature of the syngas stream is reduced by at least 100 degrees Celsius. In at least one embodiment, the syngas stream exiting the gasification process is between 800° C. and 1200° C. Preferably, the temperature of the syngas stream is reduced within a temperature range suitable for further gas treatment and/or fermentation. In various instances, the injection of at least one effluent into the syngas stream is completed to remove at least one particulate from the syngas stream.

In certain instances, the syngas stream is partially quenched. Preferably, the syngas stream is partially quenched by injecting one or more effluent into the syngas stream, the one or more effluent selected from the group consisting of microbial biomass depleted water, wastewater generated from the fermentation process, and clarified water from the wastewater treatment plant. In various embodiments, a partial quench of the syngas stream reduces the temperature of the syngas stream to 700-800° C. In various embodiments, this reduction in temperature requires approximately 1.2 tonnes of process water per 10,000 $Nm^3$ of quenched syngas, starting at 1000° C. Preferably, at least 20%, at least 30%, at least 40%, at least 50%, at least 60%, at least 70%, at least 80%, at least 90%, or substantially all of this process water is replaced through the injection of one or more effluent into the syngas stream.

In certain instances, the syngas stream is fully quenched. Preferably, the syngas stream is fully quenched by injecting one or more effluent into the syngas stream, the one or more effluent selected from the group consisting of microbial biomass depleted water, wastewater generated from the fermentation process, and clarified water from the wastewater treatment plant. In various embodiments, a full quench of the syngas stream reduces the temperature of the syngas stream to less than 300° C. In various embodiments, this reduction in temperature requires approximately 4 tonnes of process water per 10,000 $Nm^3$ of quenched syngas, starting at 1000° C. Preferably, at least 20%, at least 30%, at least 40%, at least 50%, at least 60%, at least 70%, at least 80%, at least 90%, or substantially all of this process water is replaced through the injection of one or more effluent into the syngas stream.

In particular embodiments, at least a portion of biogas generated from the wastewater treatment process is sent to the gasification process. This biogas may contain one or more component selected from the group consisting of methane, carbon dioxide, carbon monoxide, ammonia, and a sulfur compound. In various instances, this sulfur compound is hydrogen sulfide. In at least one embodiment, the biogas comprises approximately 60 percent methane and approximately 40 percent carbon dioxide. In at least one embodiment, the biogas comprises approximately 65 percent methane and approximately 35 percent carbon dioxide.

In particular embodiments, at least a portion of biogas generated from the wastewater treatment process is used as a heating source. Preferably, at least a portion of the biogas generated from the wastewater treatment process is used as a heating source by the gasification process. In various instances, at least a portion of the biogas sent to the gasification process is used as a heating source for melting at least a portion of the slag produced by the gasification process. In one or more embodiment, the biogas from the wastewater treatment process is sent to a removal process prior to being sent to the gasification process. In various instances, the removal process comprises one or more removal module capable of removing, converting and/or reducing the amount of at least one constituent in the biogas stream. Preferably, the removal process removes at least a portion of at least one sulfur compound from the biogas stream before the biogas stream is sent to the gasification process.

In particular embodiments, at least a portion of the methane within the biogas is reformed into CO and $H_2$ upon being gasified by the gasification process. In various instances, the methane reacts with the moisture contained in the syngas to produce carbon monoxide and hydrogen.

In an embodiment, at least a portion of the tail gas generated from the fermentation process, unused syngas generated by the gasification process, crude ethanol from the product recovery process, and/or fusel oil from the product recovery process are used as a heating source. Preferably, at least a portion of at least one of these effluents is used as a heating source by the gasification process. In various instances, at least a portion of at least one of these effluents is sent to the gasification process to be used as a heating source for melting at least a portion of the slag produced by the gasification process. In one or more embodiment, these effluent is treated by a removal process prior to being sent to the gasification process. In various instances, the removal process comprises one or more removal module capable of removing, converting and/or reducing the amount of at least one constituent in the effluent.

In addition to passing at least a portion of the clarified water from the wastewater treatment process to the gasification process, at least a portion of the clarified water from the wastewater treatment process may be passed to the fermentation process. In particular instances, substantially all of the clarified water from the wastewater treatment process is recycled to either the gasification process and/or the fermentation process. In certain instances, the gasification process receives at least 10%, at least 20%, at least 30%, at least 40%, at least 50%, at least 60%, at least 70%, at least 80%, at least 90%, or substantially all of the clarified water from the wastewater treatment process. In certain instances, the fermentation process receives at least 10%, at least 20%, at least 30%, at least 40%, at least 50%, at least 60%, at least 70%, at least 80%, at least 90%, or substantially all of the clarified water from the wastewater treatment process.

Preferably, the fermentation process utilizes at least a portion of the syngas from the gasification process to produce one or more fuels or chemicals. At least one of the products produced by the fermentation process may be selected from the group comprising: ethanol, acetate, butanol, butyrate, 2,3-butanediol, 1,3-butanediol, lactate, butene, butadiene, methyl ethyl ketone, ethylene, acetone, isopropanol, lipids, 3-hydroypropionate, terpenes (including but not limited to isoprene), fatty acids, 2-butanol, isobutylene, isobutanol, 1,2-propanediol, 1-propanol, and C6-C12 alcohols.

In one or more embodiment, at least a portion of the microbial biomass produced by the fermentation process may be converted to a single cell protein (SCP).

In various instances, at least a portion of the one or more fuels or chemicals is sent to a secondary conversion process. Preferably, the secondary conversion process further converts at least a portion of one or more fuels or chemicals to at least one component of diesel fuel, jet fuel, gasoline, propylene, nylon 6-6, rubber, and/or resins.

In one or more embodiment, the syngas from the gasification process is sent to a removal process prior to being sent to the fermentation process. In various instances, the removal process comprises one or more removal module capable of removing, converting and/or reducing the amount of microbe inhibitors and/or catalyst inhibitors contained in the syngas stream.

Preferably, at least one constituent removed, converted, and or reduced in the syngas stream by the removal process is selected from the group comprising: sulphur compounds, aromatic compounds, alkynes, alkenes, alkanes, olefins, nitrogen compounds, phosphorous-containing compounds, particulate matter, solids, oxygen, halogenated compounds, silicon-containing compounds, carbonyls, metals, alcohols, esters, ketones, peroxides, aldehydes, ethers, and tars.

Preferably, the removal process comprises least one removal module be selected from the group comprising: hydrolysis module, acid gas removal module, deoxygenation module, catalytic hydrogenation module, particulate removal module, chloride removal module, tar removal module, and hydrogen cyanide polishing module. In various instances, the removal process comprises at least two removal modules.

The invention may further provide for the increase and/or decrease of pressure of the syngas stream at one or more points in the process.

BRIEF DESCRIPTION OF THE DRAWINGS

FIG. 5 also shows an alternative embodiment where the enriched tail gas is directed to the process recovery process and unit to, for example, dry the product.

FIG. 6 also shows an alternative embodiment where the enriched tail gas is directed to a product recovery process and unit to, for example, dry the product.

DETAILED DESCRIPTION

Figure 1:
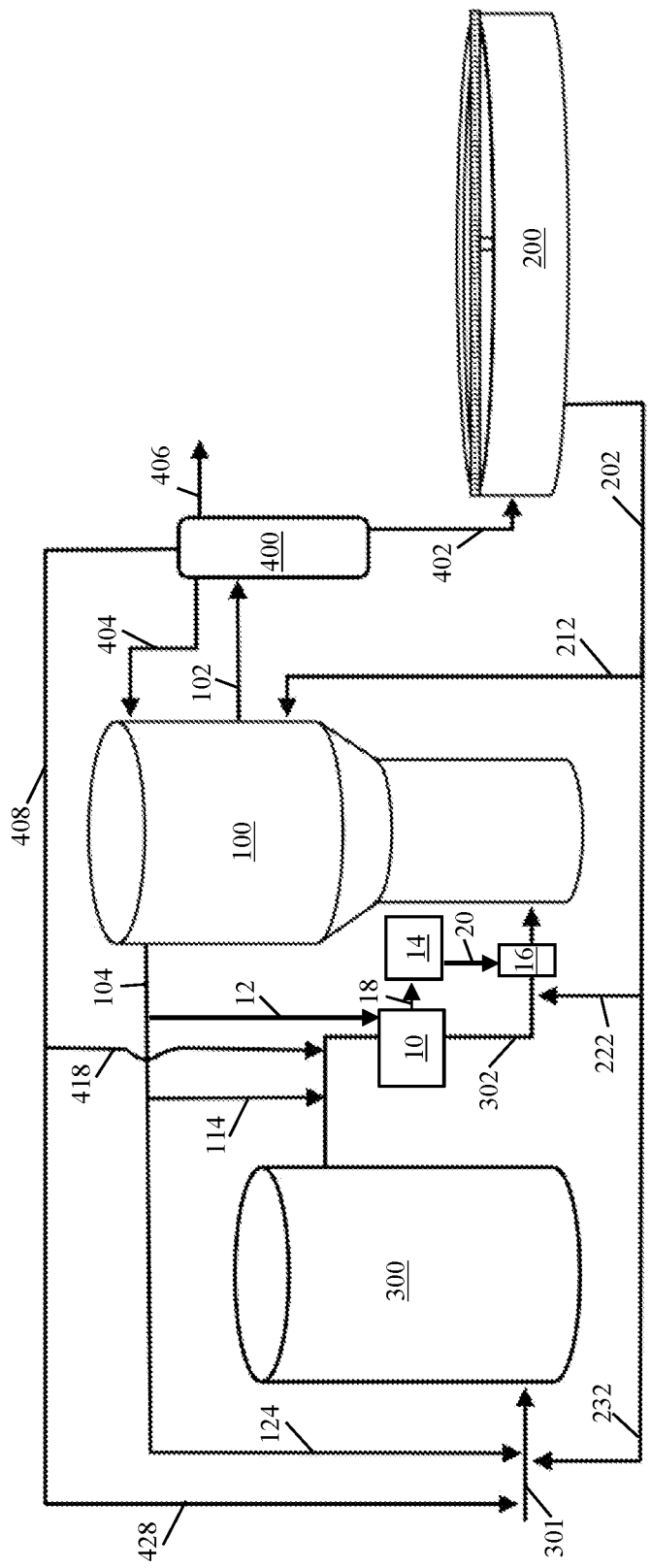
FIG. 1 shows a process integration scheme depicting the integration of a gasification process, a gas fermentation process, a product recovery process, and a wastewater treatment process, where tail gas from the gas fermentation process is used as the purge gas for an adsorption unit on a syngas stream and the enriched tail gas is conducted to a steam boiler to produce high pressure steam which is then used to power a compressor for the gas fermentation operation, in accordance with one embodiment of the invention.

The disclosure describes an integration of a gasification process and a fermentation process and optionally a wastewater treatment process. Syngas from a gasification process is passed through an adsorption unit to remove at least one tar such as a hydrocarbon or oxygenate. For ease of description, tar as used herein is meant to include sulfur compounds and nitrogen compound as well as hydrocarbons and oxygenates. Tail gas from the fermentation process is recycled to the adsorption unit to regenerate the adsorbent. The tail gas enriched in the desorbed tar is passed to a steam generation unit to generate steam. The steam may be used for a variety of purposes such for or more compressors of the gas fermentation process. Substantial unexpected benefits to the efficiencies and synergies of an integrated gasification and gas fermentation processes are achieved. Typically, tars and other impurities from an adsorbent are be desorbed using nitrogen. This technique requires production and storage of nitrogen at a cost, followed by a large volume of contaminated nitrogen which now must be treated, along with a dilute tail gas stream that has low energy value. An alternative would be to use the treated syngas to regenerate the adsorbent, and yield loss could be significant. Through using the tail gas as purge for the adsorption unit, these costs and challenges are avoided.

The terms "increasing the efficiency", "increased efficiency" and the like, when used in relation to a fermentation process, include, but are not limited to, increasing one or more of the rate of growth of microorganisms catalysing the fermentation, the growth and/or product production rate at elevated product concentrations, increasing the volume of desired product produced per volume of substrate consumed, increasing the rate of production or level of production of the desired product, increasing the relative proportion of the desired product produced compared with other by-products of the fermentation, decreasing the amount of water consumed by the process, and decreasing the amount of energy utilized by the process.

The terms "increasing the efficiency", "increased efficiency" and the like, when used in relation to the gasification process, include, but are not limited to, increasing the amount of syngas produced by the process, decreasing the amount of water supply utilized by the process, optimization of the syngas stream for gas fermentation, decreasing the greenhouse gas emissions, and decreasing the amount of energy, including but not limited to external fuel, utilized by the process.

The terms "increasing the efficiency", "increased efficiency" and the like, when used in relation to the wastewater treatment process, include, but are not limited to, decreasing the holdup time of water within the process, increasing the utilization of biogas generated by the process, decreasing the amount of effluent sent to the wastewater treatment process, decreasing the volume requirement of the process, decreasing the need for ammonia separation by the process, and decreasing the amount of energy utilized by the process.

The substrate and/or C1-carbon source may be a waste gas obtained as a byproduct of an industrial process or from some other source, such as from automobile exhaust fumes or biomass gasification. In certain embodiments, the industrial process is selected from ferrous metal products manufacturing, such as a steel mill manufacturing, non-ferrous products manufacturing, petroleum refining, coal gasification, electric power production, carbon black production, ammonia production, methanol production, and coke manufacturing. In these embodiments, the substrate and/or C1-carbon source may be captured from the industrial process before it is emitted into the atmosphere, using any convenient method. The term industrial gas is mean to include those substrates from an industrial process.

The term "fermentation", "gas fermentation" and the like should be interpreted as the process which receives one or more substrate, such as syngas produced by gasification and produces one or more product through the utilization of one or more C1-fixing microorganism. Preferably the fermentation process includes the use of one or more bioreactor. The fermentation process may be described as either "batch" or "continuous". "Batch fermentation" is used to describe a fermentation process where the bioreactor is filled with raw material, e.g. the carbon source, along with microorganisms, where the products remain in the bioreactor until fermentation is completed. In a "batch" process, after fermentation is completed, the products are extracted, and the bioreactor is cleaned before the next "batch" is started. "Continuous fermentation" is used to describe a fermentation process where the fermentation process is extended for longer periods of time, and product and/or metabolite is extracted during fermentation. Preferably the fermentation process is continuous.

The term "wastewater treatment" and the like should be interpreted as the process that separates components from the effluent from the fermentation process to produce a clarified water. The wastewater treatment process may include, but is not limited to, one or more anaerobic digesters, with varying residence times, and one or more ammonia stripping process.

The term "gasification" and the like should be interpreted as the process that converts organic and/or fossil fuel based carbonaceous materials into carbon monoxide (CO), hydrogen ($H_2$), and carbon dioxide ($CO_2$). The gasification process may include various technologies including but not limited to, counter-current fixed bed gasifiers, co-current fixed bed gasifiers, fluidized bed reactors, entrained flow gasifiers, and plasma gasifiers. The gasification process may utilize any feed, which can produce a syngas stream. The term "gasification process" encompasses the gasifier itself along with unit operations associated with gasification, including the heating source for the gasifier and syngas quench processes.

"Syngas stream", "synthesis stream" and the like refers to the gaseous substrate exiting the gasification process. The syngas stream should primarily be composed of carbon monoxide (CO), hydrogen ($H_2$), and carbon dioxide ($CO_2$). The composition of the syngas stream can vary significantly depending on the feedstock and the gasification process involved; however the typical composition of syngas includes thirty to sixty percent (30-60%) carbon monoxide (CO), twenty-five to thirty percent (25-30%) hydrogen ($H_2$), zero to five percent (0-5%) methane ($CH_4$), five to fifteen percent (5-15%) carbon dioxide ($CO_2$), plus a lesser or greater amount of water vapor, smaller amounts of sulphur compounds, hydrogen sulphide ($H_2S$), carbonyl sulphide (COS), ammonia ($NH_3$), and other trace contaminants.

In particular embodiments, the presence of hydrogen results in an improved overall efficiency of alcohol production by the fermentation process.

Syngas composition can be improved to provide a desired or optimum $H_2$:CO:$CO_2$ ratio. The syngas composition may be improved by adjusting the feedstock being fed to the gasification process. The desired $H_2$:CO:$CO_2$ ratio is dependent on the desired fermentation product of the fermentation process.

Operating the fermentation process in the presence of hydrogen has the added benefit of reducing the amount of $CO_2$ produced by the fermentation process. For example, a gaseous substrate comprising minimal $H_2$ will typically produce ethanol and $CO_2$ by the following stoichiometry [$6CO+3H_2O \rightarrow C_2H_5OH+4CO_2$]. As the amount of hydrogen utilized by the C1-fixing bacterium increases, the amount of $CO_2$ produced decreases [e.g., $2CO+4H_2 \rightarrow C_2H_5OH+H_2O$].

When CO is the sole carbon and energy source for ethanol production, a portion of the carbon is lost to $CO_2$ as follows:

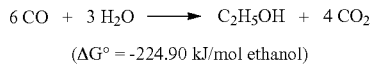

($\Delta G° = -224.90$ kJ/mol ethanol)

As the amount of $H_2$ available in the substrate increases, the amount of $CO_2$ produced decreases. At a stoichiometric ratio of 2:1 ($H_2$:CO), $CO_2$ production is completely avoided.

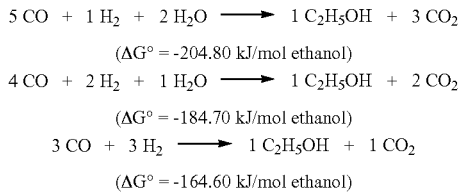

"Stream" refers to any substrate which is capable of being passed, for example, from one process to another, from one module to another, and/or from one process to a carbon capture means.

"Reactants" as used herein refer to a substance that takes part in and undergoes change during a chemical reaction. In particular embodiments, the reactants include but are not limited to CO and/or $H_2$.

"Microbe inhibitors" as used herein refer to one or more constituent that slows down or prevents a particular chemical reaction or another process including the microbe. In particular embodiments, the microbe inhibitors include, but are not limited to, oxygen ($O_2$), hydrogen cyanide (HCN), acetylene ($C_2H_2$), and BTEX (benzene, toluene, ethylbenzene, xylene).

"Catalyst inhibitor", "adsorbent inhibitor", and the like, as used herein, refer to one or more substance that decreases the rate of, or prevents, a chemical reaction. In particular embodiments, the catalyst and/or adsorbent inhibitors may include but are not limited to, hydrogen sulfide ($H_2S$) and carbonyl sulfide (COS).

"Removal process", "removal module", "clean-up module", and the like includes technologies that are capable of either converting and/or removing microbe inhibitors and/or catalyst inhibitors from the gas stream. In particular embodiments, catalyst inhibitors must be removed by an upstream removal module in order to prevent inhibition of one or more catalyst in a downstream removal module.

The term "constituents", "contaminants", and the like, as used herein, refers to the microbe inhibitors, and/or catalyst inhibitors that may be found in the gas stream. In particular embodiments, the constituents include, but are not limited to, sulphur compounds, aromatic compounds, alkynes, alkenes, alkanes, olefins, nitrogen compounds, phosphorous-containing compounds, particulate matter, solids, oxygen, halogenated compounds, silicon-containing compounds, carbonyls, metals, alcohols, esters, ketones, peroxides, aldehydes, ethers, and tars.

The term "treated gas", "treated stream" and the like refers to the gas stream that has been passed through at least one removal module and has had one or more constituent removed and/or converted.

The term "carbon capture" as used herein refers to the sequestration of carbon compounds including $CO_2$ and/or CO from a stream comprising $CO_2$ and/or CO and either:
  converting the $CO_2$ and/or CO into products; or
  converting the $CO_2$ and/or CO into substances suitable for long-term storage; or
  trapping the $CO_2$ and/or CO in substances suitable for long-term storage;
  or a combination of these processes.

The term "bioreactor", "reactor" and the like includes a fermentation device consisting of one or more vessels and/or towers or piping arrangements, which includes the Continuous Stirred Tank Reactor (CSTR), Immobilized Cell Reactor (ICR), Trickle Bed Reactor (TBR), Bubble Column, Gas Lift Fermenter, Static Mixer, a circulated loop reactor, a membrane reactor, such as a Hollow Fibre Membrane Bioreactor (HFM BR), a bubble reactor, a fine bubble reactor, a microbubble reactor, or other vessel or other device suitable for gas-liquid contact. The reactor is preferably adapted to receive a gaseous substrate comprising CO or $CO_2$ or $H_2$ or mixtures thereof. The reactor may comprise multiple reactors (stages), either in parallel or in series. For example, the reactor may comprise a first growth reactor in which the bacteria are cultured and a second fermentation reactor, to which fermentation broth from the growth reactor may be fed and in which most of the fermentation products may be produced.

"Nutrient media" or "Nutrient medium" is used to describe bacterial growth media. Preferably the fermentation process utilizes nutrient medium within the bioreactor. Generally, this term refers to a media containing nutrients and other components appropriate for the growth of a microbial culture. The term "nutrient" includes any substance that may be utilized in a metabolic pathway of a microorganism. Exemplary nutrients include potassium, B vitamins, trace metals, and amino acids.

The term "fermentation broth" or "broth" is intended to encompass the mixture of components including nutrient media and a culture or one or more microorganisms. Preferably the fermentation process utilizes fermentation broth to ferment the syngas stream to one or more product.

The term "acid" as used herein includes both carboxylic acids and the associated carboxylate anion, such as the mixture of free acetic acid and acetate present in a fermentation broth as described herein. The ratio of molecular acid to carboxylate in the fermentation broth is dependent upon the pH of the system. In addition, the term "acetate" includes both acetate salt alone and a mixture of molecular or free acetic acid and acetate salt, such as the mixture of acetate salt and free acetic acid present in a fermentation broth as described herein.

The term "desired composition" is used to refer to the desired level and types of components in a substance, such as, for example, of a gas stream, including but not limited to syngas. More particularly, a gas is considered to have a "desired composition" if it contains a particular component (e.g. CO, $H_2$, and/or $CO_2$) and/or contains a particular component at a particular proportion and/or does not contain a particular component (e.g. a contaminant harmful to the microorganisms) and/or does not contain a particular component at a particular proportion. More than one component may be considered when determining whether a gas stream has a desired composition.

Unless the context requires otherwise, the phrases "fermenting", "fermentation process" or "fermentation reaction" and the like, as used herein, are intended to encompass both the growth phase and product biosynthesis phase of the gaseous substrate.

A "microorganism" is a microscopic organism, especially a bacterium, archea, virus, or fungus. The microorganism of the invention is typically a bacterium. As used herein, recitation of "microorganism" should be taken to encompass "bacterium." It should be noted that the term microorganism and the term bacteria are used interchangeably throughout the document.

A "parental microorganism" is a microorganism used to generate a microorganism of the invention. The parental microorganism may be a naturally-occurring microorganism (e.g., a wild-type microorganism) or a microorganism that has been previously modified (e.g., a mutant or recombinant microorganism). The microorganism of the invention may be modified to express or overexpress one or more enzymes that were not expressed or overexpressed in the parental microorganism. Similarly, the microorganism of the invention may be modified to contain one or more genes that were not contained by the parental microorganism. The microorganism of the invention may also be modified to not express or to express lower amounts of one or more enzymes that were expressed in the parental microorganism. In one embodiment, the parental microorganism is *Clostridium autoethanogenum*, *Clostridium ljungdahlii*, or *Clostridium ragsdalei*. In a preferred embodiment, the parental microorganism is *Clostridium autoethanogenum* LZ1561, which was deposited on Jun. 7, 2010, with Deutsche Sammlung von Mikroorganismen and Zellkulturen GmbH (DSMZ) located at InhoffenstraBe 7B, D-38124 Braunschweig, Germany on Jun. 7, 2010, under the terms of the Budapest Treaty and accorded accession number DSM23693. This strain is described in International Patent Application No. PCT/NZ2011/000144, which published as WO 2012/015317.

The term "derived from" indicates that a nucleic acid, protein, or microorganism is modified or adapted from a different (e.g., a parental or wild-type) nucleic acid, protein, or microorganism, so as to produce a new nucleic acid, protein, or microorganism. Such modifications or adaptations typically include insertion, deletion, mutation, or substitution of nucleic acids or genes. Generally, the microorganism of the invention is derived from a parental microorganism. In one embodiment, the microorganism of the invention is derived from *Clostridium autoethanogenum*, *Clostridium ljungdahlii*, or *Clostridium ragsdalei*. In a preferred embodiment, the microorganism of the invention is derived from *Clostridium autoethanogenum* LZ1561, which is deposited under DSMZ accession number DSM23693.

"Wood-Ljungdahl" refers to the Wood-Ljungdahl pathway of carbon fixation as described, e.g., by Ragsdale, *Biochim Biophys Acta*, 1784: 1873-1898, 2008. "Wood-Ljungdahl microorganisms" refers, predictably, to microorganisms containing the Wood-Ljungdahl pathway. Generally, the microorganism of the invention contains a native Wood-Ljungdahl pathway. Herein, a Wood-Ljungdahl pathway may be a native, unmodified Wood-Ljungdahl pathway or it may be a Wood-Ljungdahl pathway with some degree of genetic modification (e.g., overexpression, heterologous expression, knockout, etc.) so long as it still functions to convert CO, $CO_2$, and/or $H_2$ to acetyl-CoA.

"C1" refers to a one-carbon molecule, for example, CO, $CO_2$, $CH_4$, or $CH_3OH$. "C1-oxygenate" refers to a one-carbon molecule that also comprises at least one oxygen atom, for example, CO, $CO_2$, or $CH_3OH$. "C1-carbon source" refers a one carbon-molecule that serves as a partial or sole carbon source for the microorganism of the invention. For example, a C1-carbon source may comprise one or more of CO, $CO_2$, $CH_4$, $CH_3OH$, or $CH_2O_2$. Preferably, the C1-carbon source comprises one or both of CO and $CO_2$. A "C1-fixing microorganism" is a microorganism that has the ability to produce one or more products from a C1-carbon source. Typically, the microorganism of the invention is a C1-fixing bacterium.

An "anaerobe" is a microorganism that does not require oxygen for growth. An anaerobe may react negatively or even die if oxygen is present above a certain threshold. However, some anaerobes are capable of tolerating low levels of oxygen (e.g., 0.000001-5% oxygen). Typically, the microorganism of the invention is an anaerobe.

"Acetogens" are obligately anaerobic bacteria that use the Wood-Ljungdahl pathway as their main mechanism for energy conservation and for the synthesis of acetyl-CoA and acetyl-CoA-derived products, such as acetate (Ragsdale, *Biochim Biophys Acta*, 1784: 1873-1898, 2008). In particular, acetogens use the Wood-Ljungdahl pathway as a (1) mechanism for the reductive synthesis of acetyl-CoA from $CO_2$, (2) terminal electron-accepting, energy conserving process, (3) mechanism for the fixation (assimilation) of $CO_2$ in the synthesis of cell carbon (Drake, Acetogenic Prokaryotes, In: The Prokaryotes, 3rd edition, p. 354, New York, N.Y., 2006). All naturally occurring acetogens are C1-fixing, anaerobic, autotrophic, and non-methanotrophic. Typically, the microorganism of the invention is an acetogen.

An "ethanologen" is a microorganism that produces or is capable of producing ethanol. Typically, the microorganism of the invention is an ethanologen.

An "autotroph" is a microorganism capable of growing in the absence of organic carbon. Instead, autotrophs use inorganic carbon sources, such as CO and/or $CO_2$. Typically, the microorganism of the invention is an autotroph.

A "carboxydotroph" is a microorganism capable of utilizing CO as a sole source of carbon and energy. Typically, the microorganism of the invention is a carboxydotroph.

A "methanotroph" is a microorganism capable of utilizing methane as a sole source of carbon and energy. In certain embodiments, the microorganism of the invention is a methanotroph or is derived from a methanotroph. In other embodiments, the microorganism of the invention is not a methanotroph or is not derived from a methanotroph.

"Substrate" refers to a carbon and/or energy source for the microorganism of the invention. Typically, the substrate is gaseous and comprises a C1-carbon source, for example, CO, $CO_2$, and/or $CH_4$. Preferably, the substrate comprises a C1-carbon source of CO or $CO+CO_2$. The substrate may further comprise other non-carbon components, such as $H_2$ or $N_2$.

The term "co-substrate" refers to a substance that, while not necessarily being the primary energy and material source for product synthesis, can be utilized for product synthesis when added to another substrate, such as the primary substrate.

The composition of the substrate may have a significant impact on the efficiency and/or cost of the reaction. For example, the presence of oxygen ($O_2$) may reduce the efficiency of an anaerobic fermentation process. Depending on the composition of the substrate, it may be desirable to treat, scrub, or filter the substrate to remove any undesired impurities, such as toxins, undesired components, or dust particles, and/or increase the concentration of desirable components.

In certain embodiments, the fermentation is performed in the absence of carbohydrate substrates, such as sugar, starch, lignin, cellulose, or hemicellulose.

The microorganism of the invention may be cultured with the gas stream to produce one or more products. For instance, the microorganism of the invention may produce or may be engineered to produce ethanol (WO 2007/117157), acetate (WO 2007/117157), butanol (WO 2008/115080 and WO 2012/053905), butyrate (WO 2008/115080), 2,3-butanediol (WO 2009/151342 and WO 2016/094334), lactate (WO 2011/112103), butene (WO 2012/024522), butadiene (WO 2012/024522), methyl ethyl ketone (2-butanone) (WO 2012/024522 and WO 2013/185123), ethylene (WO 2012/026833), acetone (WO 2012/115527), isopropanol (WO 2012/115527), lipids (WO 2013/036147), 3-hydroxypropionate (3-HP) (WO 2013/180581), terpenes, including isoprene (WO 2013/180584), fatty acids (WO 2013/191567), 2-butanol (WO 2013/185123), 1,2-propanediol (WO 2014/036152), 1-propanol (WO 2014/0369152), chorismate-derived products (WO 2016/191625), 3-hydroxybutyrate (WO 2017/066498), and 1,3-butanediol (WO 2017/0066498). In certain embodiments, microbial biomass itself may be considered a product. These products may be further converted to produce at least one component of diesel, jet fuel, and/or gasoline. Additionally, the microbial biomass may be further processed to produce a single cell protein (SCP).

A "single cell protein" (SCP) refers to a microbial biomass that may be used in protein-rich human and/or animal feeds, often replacing conventional sources of protein supplementation such as soymeal or fishmeal. To produce a single cell protein or other product, the process may comprise additional separation, processing, or treatments steps. For example, the method may comprise sterilizing the microbial biomass, centrifuging the microbial biomass, and/or drying the microbial biomass. In certain embodiments, the microbial biomass is dried using spray drying or paddle drying. The method may also comprise reducing the nucleic acid content of the microbial biomass using any method known in the art, since intake of a diet high in nucleic acid content may result in the accumulation of nucleic acid degradation products and/or gastrointestinal distress. The single cell protein may be suitable for feeding to animals, such as livestock or pets. In particular, the animal feed may be suitable for feeding to one or more beef cattle, dairy cattle, pigs, sheep, goats, horses, mules, donkeys, deer, buffalo/bison, llamas, alpacas, reindeer, camels, bantengs, gayals, yaks, chickens, turkeys, ducks, geese, quail, guinea fowl, squabs/pigeons, fish, shrimp, crustaceans, cats, dogs, and rodents. The composition of the animal feed may be tailored to the nutritional requirements of different animals. Furthermore, the process may comprise blending or combining the microbial biomass with one or more excipients.

An "excipient" may refer to any substance that may be added to the microbial biomass to enhance or alter the form, properties, or nutritional content of the animal feed. For example, the excipient may comprise one or more of a carbohydrate, fiber, fat, protein, vitamin, mineral, water, flavor, sweetener, antioxidant, enzyme, preservative, probiotic, or antibiotic. In some embodiments, the excipient may be hay, straw, silage, grains, oils or fats, or other plant material. The excipient may be any feed ingredient identified in Chiba, Section 18: Diet Formulation and Common Feed Ingredients, Animal Nutrition Handbook, $3^{rd}$ revision, pages 575-633, 2014.

A "native product" is a product produced by a genetically unmodified microorganism. For example, ethanol, acetate, and 2,3-butanediol are native products of *Clostridium autoethanogenum*, *Clostridium ljungdahlii*, and *Clostridium ragsdalei*. A "non-native product" is a product that is produced by a genetically modified microorganism but is not produced by a genetically unmodified microorganism from which the genetically modified microorganism is derived.

"Selectivity" refers to the ratio of the production of a target product to the production of all fermentation products produced by a microorganism. The microorganism of the invention may be engineered to produce products at a certain selectivity or at a minimum selectivity. In one embodiment, a target product accounts for at least about 5%, 10%, 15%, 20%, 30%, 50%, or 75% of all fermentation products produced by the microorganism of the invention. In one embodiment, the target product accounts for at least 10% of all fermentation products produced by the microorganism of the invention, such that the microorganism of the invention has a selectivity for the target product of at least 10%. In another embodiment, the target product accounts for at least 30% of all fermentation products produced by the microorganism of the invention, such that the microorganism of the invention has a selectivity for the target product of at least 30%.

The culture is generally maintained in an aqueous culture medium that contains nutrients, vitamins, and/or minerals sufficient to permit growth of the microorganism. Preferably the aqueous culture medium is an anaerobic microbial growth medium, such as a minimal anaerobic microbial growth medium.

The culture/fermentation should desirably be carried out under appropriate conditions for production of the target product. Typically, the culture/fermentation is performed under anaerobic conditions. Reaction conditions to consider include pressure (or partial pressure), temperature, gas flow rate, liquid flow rate, media pH, media redox potential, agitation rate (if using a continuous stirred tank reactor), inoculum level, maximum gas substrate concentrations to ensure that gas in the liquid phase does not become limiting, and maximum product concentrations to avoid product inhibition. In particular, the rate of introduction of the substrate may be controlled to ensure that the concentration of gas in the liquid phase does not become limiting, since products may be consumed by the culture under gas-limited conditions.

Operating a bioreactor at elevated pressures allows for an increased rate of gas mass transfer from the gas phase to the liquid phase. Accordingly, it is generally preferable to perform the culture/fermentation at pressures higher than atmospheric pressure. Also, since a given gas conversion rate is, in part, a function of the substrate retention time and retention time dictates the required volume of a bioreactor, the use of pressurized systems can greatly reduce the volume of the bioreactor required and, consequently, the capital cost of the culture/fermentation equipment. This, in turn, means that the retention time, defined as the liquid volume in the bioreactor divided by the input gas flow rate, can be reduced when bioreactors are maintained at elevated pressure rather than atmospheric pressure. The optimum reaction conditions will depend partly on the particular microorganism used. However, in general, it is preferable to operate the fermentation at a pressure higher than atmospheric pressure. Also, since a given gas conversion rate is in part a function of substrate retention time and achieving a desired retention time, in turn, dictates the required volume of a bioreactor, the use of pressurized systems can greatly reduce the volume of the bioreactor required, and consequently the capital cost of the fermentation equipment.

Target products may be separated or purified from a fermentation broth using any suitable removal process, which may utilize a method or combination of methods known in the art, including, for example, fractional distillation, vacuum distillation, evaporation, pervaporation, gas stripping, phase separation, and extractive fermentation, including, for example, liquid-liquid extraction. In certain embodiments, target products are recovered from the fermentation broth by continuously removing a portion of the broth from the bioreactor, separating microbial cells from the broth (conveniently by filtration), and recovering one or more target products from the broth. Alcohols and/or acetone may be recovered, for example, by distillation. Acids may be recovered, for example, by adsorption on activated charcoal. Separated microbial cells may be returned to the bioreactor. The cell-free permeate remaining after target products have been removed may also be returned to the bioreactor. Additional nutrients (such as B vitamins) may be added to the cell-free permeate to replenish the medium before it is returned to the bioreactor.

"Enriched" refers to a stream having an increased amount of a component as compared the stream prior to the enriching step.

Description

This disclosure shows that by integrating the gasification operation and the fermentation operation into an integrated system, unexpected synergies result in the overall efficiency of the integrated system being improved. More specifically, the disclosure identifies an integration where syngas from a gasification process is treated using an adsorbent to remove at least one tar, such as a hydrocarbon or oxygenate, and the tail gas of the fermentation operation is used to regenerate adsorbent thereby becoming enriched in tar and increased in calorific value. The enriched tail gas may be combusted in a steam generation unit to generate steam which can be used for many different purposes. Once such use that provides further integration is to use the steam to generate power that then powers a compressor of the gas fermentation process.

Syngas produced by gasification of biomass or waste feedstocks contains hydrocarbons and oxygenates commonly known as tars, the production and concentration of which is related to the feedstock and the temperature of the gasification process. Typically, in a gasifier where air is used as the oxidant, the temperature is lower compared to a process where enriched air or purified oxygen is used as the oxidant. Low temperature gasifiers produce a syngas which produces a significant concentration of tar, such as 1000 to 10,000 ppmv, and also methane, 1 to 5 vol. %. The tars and methane are undesirable products for gas fermentation. Neither are fermentable, and the tars in particular, should be removed for operation of the gas fermentation process.

Removal of the heavier, higher boiling point, tars can be performed by cooling the syngas which condenses these tars along with water present in the syngas. This liquid product, the condensate, comprising one or more of hydrocarbons, oxygenates, and or water, is a waste product which often requires disposal. In some embodiments where a large quantity of condensate is produced and a single component of the condensate is of a significant concentration, it may be desirable and economical to purify that component for sale. In another embodiment, a disposal technique for the condensate is combustion. The condensate may be combusted by use of a flame produced by combustion of fuel gas, natural gas, syngas, or, a fermentation tail gas obtained from a gas fermentation process. Alternatively, the condensate may be passed to the wastewater treatment process for disposal, which results in increased yield as compared to combusting the condensate. The use of fermentation tail gas, which may comprise methane and residual CO and $H_2$, is ideal in that the tail gas is low cost and often is also a waste stream which may require disposal. The use of fermentation tail gas is further uniquely suited to this integration due to any methane content of the syngas which may pass through to the tail gas and operate to increases the calorific value of the tail gas thus increasing the value of the tail as a combustible stream.

In other embodiments, such as in the low temperature gasification embodiments, both significant quantities of condensate and methane in syngas are present, and thus the resulting tail gas is of significant value for combustion. However, some gasification processes, such as high temperature gasification processes, may result in a syngas which contains very little tar or methane, for example <0.5% in one embodiment, or down to 0.1 mol % in another embodiment, and results in a fermentation tail gas which may be too dilute to be combusted. In this embodiment there is very little or no condensate which requires disposal. Desorption of tars and oxygenates using a fermentation tail gas stream which thereby enriches the fermentation tail gas energy density provides a opportunity to use what would otherwise be a low value tail gas in a higher value generation setting. For example, instead of adding methane to flare the tail gas, the enriched tail gas, after desorption of tars and oxygenates, may be used by a steam boiler or even a power generation unit such as a cogeneration unit or a direct generation unit. The enriched fermentation tail gas has added energy value which improves the combustion efficiency when used for a steam boiler or a power generation unit or the like. A further efficiency is achieved since in the absence of using the tail gas to desorb the hydrocarbons and oxygenates from the adsorbent, nitrogen may need to be obtained and used to desorb and regenerate the adsorbent. Using an internal process stream provides for cost reduction.

Lighter tars, with lower boiling points, such as benzene, toluene, ethylbenzene, and xylene (BTEX), may also be present in the syngas from the gasification process or in the industrial gas and should be removed prior to gas fermentation. BTEX may be removed by an adsorption unit such as a temperature swing adsorption (TSA) unit or pressure swing adsorption (PSA). A second use of fermentation tail gas is as a purge gas to desorb BTEX from the adsorption beds. After being used as a purge gas, the tail gas comprises residual syngas components (CH4, CO, H2) and is enriched in desorbed BTEX, thus forming an enriched tail gas that contains a significant recoverable energy. The enriched tail gas stream, in addition to the remaining fermentation tail gas, may be combusted in a steam boiler to produce steam, such as high pressure stream, suitable for a variety of process units including those used in the gasification and gas fermentation system.

There is a surprisingly large quantity of residual energy in the enriched tail gas, and thus a surprising amount of steam produced from the enriched tail gas. In one embodiment, an air-blown gasification system, 75% of the chemical energy contained in the feedstock may be recovered as syngas, 20% (15% of the feedstock, 20% of 75%) of which may be present as BTEX, methane, and other light hydrocarbons and 80% as CO and $H_2$. For 1 dry tonne of feed having a lower heating value of 18 GJ/tonne, this means 3 GJ would be present as unfermentable species, equivalent to approximately 1.2 tonnes of steam production. As compared to a syngas stream from a gasification process or the industrial waste gas, the enriched tail gas is enriched in $N_2$; enriched in $CO_2$; depleted in impurities; or any combination thereof resulting in the enriched tail gas providing an unexpected improvement in the desorption of adsorbed components. The steam produced may be used for: distillation of fermentation products, operation of an adsorption chiller, steam driven compression, evaporation of waste water, drying of biocatalyst, team in Place (SIP), Clean in Place (CIP), drying of feedstock, steam driven feedstock conveyers, heating of buildings, and power generation. An additional degree of integration may be achieved when the steam produced is used for power generation and the power is used to power a compressor of the gas fermentation process.

Other embodiments include one or more effluents selected from biogas generated from a wastewater treatment process, tail-gas generated from the fermentation process, unused syngas generated by the gasification process, microbial biomass generated from the fermentation process, microbial biomass generated from a wastewater treatment process, crude ethanol from the product recovery process, fusel oil from the product recovery process, microbial biomass depleted water, wastewater generated from the fermentation process, and clarified water from a wastewater treatment process, which may be sent to the gasification process to produce a syngas stream, used by the gasification process as a heating source, and/or used by the gasification process to quench the syngas stream. The syngas stream is preferably suitable for gas fermentation.

These various effluents are produced either in or downstream of, the fermentation process. The fermentation process produces a wastewater stream that contains organic metabolites, such as microbial biomass, ethanol, acetate, and 2-3 butanediol, and various inorganic compounds such as salts and trace metals. This wastewater stream is often sent to a wastewater treatment process. A typical wastewater treatment process includes the following steps: (i) separation of the microbial biomass, which is a suspended solid; (ii) concentration of the microbial biomass solids in a separate long residence time, approximately thirty days, anaerobic digester; (iii) concentration of the clarified effluent, with reduced amounts of microbial biomass solids, containing soluble organics, in a shorter residence time, approximately two to three days, anaerobic digester. Typically, these anaerobic digesters consumer a majority, preferably greater than eighty percent (80%) of the organic matter in the feed and produce a biogas product. The biogas product is composed primarily of methane ($CH_4$) and carbon dioxide ($CO_2$).

This biogas product may be useful for power generation. However, to use the biogas for power generation, the biogas typically must be treated by one or more removal modules. Furthermore, as later illustrated, use of microbial biomass to produce biogas was found to be a relatively low-value use of the microbial biomass when compared to the opportunities for gasifying or drying the microbial biomass.

In addition to the aforementioned steps, the wastewater treatment process may also include additional treatment steps following the anaerobic digesters. Typically, the treated effluent from the anaerobic digesters is subjected to additional treatment including, aerobic treatment, struvite recovery, nitrogen recovery, and in some instances reverse osmosis. The clarified water produced by the wastewater treatment process is suitable for re-use and/or discharge. One suitable way to use this clarified water is to recycle the clarified water to the fermentation process and/or the gasification process.

Although the wastewater treatment process is capable of successfully treating the wastewater from the fermentation process to produce clarified water, the organic metabolites in the wastewater stream often pose several challenges. Specifically, the treatment of the microbial biomass in the wastewater stream by the wastewater treatment process can pose design challenges due to (i) the high protein content and thus high ammonia generation during anaerobic digestion, and (ii) the large plot space required to house the wastewater treatment process.

Ammonia poses a challenge to anaerobic digestion because ammonia is associated with inhibiting methanogenesis during the anaerobic digestion process if it is in high concentrations. Inhibitory concentrations of ammonia have been found to be in the range of 2 to 3 g/L. This threshold can be greatly surpassed, as digestion of separated microbial biomass can result in ammonia concentrations greater than 20 g/L. Thus, in order to process the microbial biomass by a wastewater treatment process, an ammonia stripping process is often required to lower the ammonia concentration below the inhibitory levels.

A large plot space requirement poses a significant issue in localities where land is at a premium. Each component of the wastewater treatment process requires a substantial amount of space due to the significant volumes that are processed. For example, the long residence time anaerobic digester can, in some instances, exceed 7,000 $m^3$.

The inventors have found that by recycling at least a portion of the microbial biomass to the gasification process these challenges can be overcome. With less microbial biomass being sent to anaerobic digestion, less ammonia is produced and therefore the need for an ammonia stripping process is reduced and/or eliminated. Additionally, as larger volumes of effluent from the fermentation process are sent to the gasification process, lesser volumes of effluent are sent to the wastewater treatment process. With lesser volumes of effluent being processed by the wastewater treatment process, the required volume and corresponding plot space requirements are reduced, making the design advantageous for localities where land is at a premium.

In addition to overcoming the aforementioned challenges, recycling microbial biomass to the gasification process provides the following advantageous results: (i) a greater portion of energy contained in the biomass is recovered; (ii) the $H_2:CO$ ratio within the resulting syngas stream is increased; (iii) the inorganic content, metal compounds, and alkali elements in the microbial biomass, which normally would require additional treatment steps by the wastewater treatment process, are conveniently collected in the gasification process as part of the ash fraction, which already requires disposal, thus overall waste treatment is reduced; and (iv) the nitrogen contained within the biomass will undergo reaction in the gasifier to become $N_2$, $NH_3$, and trace HCN, which integrates well with existing removal processes.

The inventors have also surprisingly found revenue gain when recycling biomass to gasification when compared to the use of biomass in the production of biogas. Specifically, the inventors have found a 321% gain in revenue when comparing the utilization of biomass in syngas versus the utilization of biomass in the production of biogas.

This percentage of revenue gain is best illustrated in the table below. The Table shows the value generated from 20 GJ/hr of biomass, as taken through each pathway.

is the GJ/hr Product Gas multiplied by the $/GJ Product Value. The % Revenue Gain is the comparative value of $/hr Revenue for the Anaerobic Digestion to Biogas versus the $/hr Revenue for the Gasification to Syngas. The $GJ Biomass Value illustrates the value of the biomass given the process selected. This is calculated by dividing the $/hr Revenue by the GJ/hr Biomass. As shown, the utilization of biomass to produce syngas through gasification greatly improves both revenue and value of the biomass.

An additional benefit of feeding the microbial biomass to the gasification process is that the microbial biomass may help provide supplementary amounts of syngas that may be needed in order to adequately supply the fermentation process. For example, a gasifier feed rate of approximately 1,200 dry tonnes per day, equivalent to 50 dry tonnes per hour, is required to supply the syngas needed for a 100,000 tonne/year ethanol production fermentation process, based upon current design parameters. The biomass produced by a fermentation process of this scale is typically between 1,000 and 1,200 kg/hr. This amount of biomass is substantial. The supplementary amounts of syngas that can be produced by gasification of biomass may be particularly beneficial in situations where gasifier feedstock is limited or where the feedstock price is high.

The biomass produced by the fermentation process may need an additional drying step before being passed to the gasifier in order to increase the percentage of biomass content. Depending on the requirements of the gasifier, the biomass may need to be dried to the point where the biomass makes up greater than 20 wt. %.

TABLE

| | GJ/hr Biomass | GJ/hr Product Gas | GJ/hr Ethanol | $/GJ Product Value | $/hr Revenue | % Revenue Gain | $GJ Biomass Value |
|---|---|---|---|---|---|---|---|
| Anaerobic Digestion to Biogas | 20 | 12 | n/a | 8 | 96.0 | n/a | 4.80 |
| Gasification to Syngas | 20 | 15 | 8.25 | 37.3 | 307.7 | 321% | 15.39 |

The calculations shown in the above table compare the conversion value of biomass to biogas, via anaerobic digestion, versus biomass to syngas, via gasification. The conversion efficiency of producing biogas from biomass via anaerobic digestion is approximately sixty percent (60%). The conversion efficiency of producing syngas from biomass via gasification is approximately seventy-five percent (75%), which can vary depending on the gasification technology used. The GJ/hr Product Gas represents the GJ/hr Biomass multiplied by the respective conversion efficiency. The GJ/hr Ethanol represents the GJ/hr Product Gas multiplied by the conversion efficiency of gas fermentation. The conversion efficiency of gas fermentation for the production of ethanol is approximately, fifty-five percent (55%), conservatively. With this conversion efficiency, the GJ/hr Ethanol was found to be 8.25. The current price of biogas where no renewable incentives exist is in the range of four dollars ($4) in the United States to ten dollars ($10) in the European Union, as of Nov. 5, 2018. For analysis purposes, a price of eight dollars per gigajoule biogas ($8/GJ Product Value) is used. The price of low carbon ethanol is currently, as of Nov. 5, 2018, $850/tonne ethanol in the European Union, $1100/tonne ethanol in China, and $1200/tonne ethanol in the United States. For analysis purposes, a price of $1000/tonne ethanol, equivalent to $37.30/GJ, is used. The $/hr Revenue However, gasifying biomass with increased moisture content has the added benefit of increasing the $H_2:CO$ ratio in the syngas produced. At approximately 15 wt. % moisture in the gasification feedstock, the resulting syngas stream comprises an $H_2:CO$ ratio of 1:1. When the moisture in the gasification feedstock is increased to 40 wt. %, the resulting syngas stream comprises an $H_2:CO$ ratio of 2:1. As previously stated, increased $H_2:CO$ ratio in the syngas stream being fed to the fermentation process results in an increased efficiency of the fermentation process.

The substrate and/or C1-carbon source may be a waste gas obtained as a byproduct of an industrial process or from another source, such as automobile exhaust fumes, biogas or landfill gas or from electrolysis. The substrate and/or C1-carbon source may be syngas generated by pyrolysis, torrefaction, or gasification. In other words, waste material may be recycled by pyrolysis, torrefaction, or gasification to generate syngas which is used as the substrate and/or C1-carbon source. In certain embodiments, the industrial process is selected from ferrous metal products manufacturing, such as a steel mill manufacturing, non-ferrous products manufacturing, petroleum refining, electric power production, carbon black production, paper and pulp manufacturing, ammonia production, methanol production, coke manufacturing, or any combination thereof. In these embodiments, the substrate and/or C1-carbon source may be captured from the industrial process before it is emitted into the atmosphere, using any known method. The substrate and/or C1-carbon source may be syngas, such as syngas obtained by gasification of coal, gasification of refinery residues, gasification of biomass, gasification of lignocellulosic material, black liquor gasification, gasification of municipal solid waste, gasification of industrial solid waste, gasification of sewerage, gasification of sludge from wastewater treatment, reforming of natural gas, reforming of biogas, reforming of landfill gas or any combination thereof. Examples of municipal solid waste include tires, plastics, and fibers in sholes, apparel, textiles. The municipal solid waste may be sorted or unsorted. Examples of biomass may include lignocellulosic material and may also include microbial biomass. Lignocellulosic material may include agriculture waste and forest waste.

The figures discussed below first address processes and apparatus involving gasification, and then address processes and apparatus where gasification to produce syngas is not required. In all cases, the tail gas from the fermentation is used to desorb at least one component from the adsorbent thereby enriching the tail gas. The enriched tail gas has multiple possible uses. The tail gas from the fermentation further surprisingly performs as a better desorbent than for example an untreated synthesis gas.

FIG. 1 shows a process integration scheme depicting the integration of a gasification process 300 having a gas fermentation process 100, a product recovery process 400, and a wastewater treatment process 200, in accordance with one embodiment of the invention. These processes are integrated in a way that provides surprising synergies and advantages. The gasification process 300 receives a gasification feed 301, which may be any suitable material capable of being gasified to produce a syngas stream 302. In various instances, the gasification feed 301 is comprised at least partially of sorted and/or unsorted municipal solid waste. In other instances, the gasification feed 301 is comprised at least partially of forest and/or agricultural waste. In particular embodiments, the gasification feed 301 is comprised of a combination of two or more of the following: sorted municipal solid waste, unsorted municipal solid waste, forest waste, agricultural waste, at least one effluent from the fermentation process 100, at least one effluent from the product recovery process 400, and at least one effluent from the wastewater treatment process 200.

The gasification process 300 receives the gasification feed 301 and produces a syngas stream 302 that is suitable for fermentation by a gas fermentation process 100. The fermentation process 100 utilizes this stream as a carbon source for producing one or more product, which may be at least partially contained in one or more effluent stream 102, 104. In various instances, the effluent from the fermentation process 100 is fermentation broth. However, certain components of the syngas are to be removed in an adsorption unit 10 before the syngas is fermented in the fermentation process 300. Components removed include at least one of a hydrocarbon, an oxygenate, a sulfur compound, and or nitrogen compound. The component is adsorbed onto the adsorbent of the adsorption unit. The adsorption unit may be a temperature swing adsorption system, a pressure swing adsorption system, a swing bed system, a moving bed system, or a fixed bed system. Over time the adsorbent may reach capacity and need regeneration. A desorbent and or purge gas is helpful to regenerate the adsorbent. As described above, a further integration of the gasification process and the gas fermentation process is to use at least a portion of tail gas 104 of fermentation process 100 as the desorbent or purge as 12 for the adsorption unit 10. The tail gas used as desorbent or purge 12 for the adsorption unit 10 becomes enriched in components desorbed from the adsorbent including the at least one hydrocarbon, oxygenate, sulfur compound and or nitrogen compound to form an enriched tail gas 18 that has a higher calorific value than stream 12. In this embodiment, enriched tail gas 18 is conducted to steam boiler 14 to generate high pressure steam 20. High pressure steam 20 is provided to system 16 which generates power from the high-pressure steam and powers a compressor which compresses the syngas before the syngas is introduced to the gas fermentation process 100.

One or more products produced by the fermentation process 100 is removed and/or separated from the fermentation broth by a product recovery process 400. Preferably, the product recovery process 400 removes one or more products 406 and produces at least one effluent 402, 404, 408, which comprise reduced amounts of at least one product. This effluent may be sent via a conduit 402 to the wastewater treatment process 200 to produce at least one effluent 202, which may be recycled to the gasification process 300 and/or the fermentation process 100.

An effluent from the fermentation process 100 is tail gas generated by the fermentation process 100. At least a portion of this tail gas may be sent via a conduit 104, 124, and 125 to the gasification process 300. A portion of the pail gas is conducted in line 12 for use as a desorbent and or purge gas for adsorption unit 10. In an optional embodiment, at least a portion of the tail gas may be sent by a conduit 124 to the gasification process 300 to be used as part of the gasification feed 301. In another optional embodiment, at least a portion of the tail gas may be sent via a conduit 114 to the gasification process 300 to quench the syngas stream 302.

In at least one embodiment, the effluent from the fermentation process 100 is fermentation broth. At least a portion of the fermentation broth is sent via a conduit 102 to the product recovery process 400. In at least one embodiment, the product recovery process 400 separates at least a portion of the microbial biomass from the fermentation process 100. In various embodiments, at least a portion of the microbial biomass that is separated from the fermentation broth is recycled to the fermentation process 100 via a conduit 404. In various embodiments, at least a portion of the microbial biomass that is separated from the fermentation broth is sent via a conduit 428 to the gasification process 300. At least a portion of the microbial biomass may be used as part of the gasification feed 301.

In various optional embodiments, at least a portion of a wastewater stream, comprising fermentation broth, which may contain microbial biomass, from the fermentation process 100 may be sent directly via a conduit 104 to the gasification process 300, without being passed to the product recovery process 400. At least a portion of the wastewater may be sent by a conduit 124 to the gasification process 300 to be used as part of the gasification feed 301. At least a portion of the fermentation broth may be sent via a conduit 114 to the gasification process 300 to quench the syngas stream 302.

In instances where the fermentation broth is processed by the product recovery process 400, at least a portion of the microbial biomass depleted water, produced through the removal of microbial biomass from the fermentation broth, may be returned to the fermentation process 100 via a conduit 404 and/or sent via a conduit 408 to the gasification process 300. At least a portion of the microbial biomass depleted water may be sent via a conduit 428 to the gasification process 300 to be used as part of the gasification feed 301. At least a portion of the microbial biomass depleted water may be sent via a conduit 418 to quench the syngas stream 302. Additionally, at least a portion of the effluent from the product recovery process 400 may be sent via a conduit 402 to the wastewater treatment process 200. Preferably, the effluent from the product recovery process 400 comprises reduced amounts of product and/or microbial biomass.

Preferably, the wastewater treatment process 200 receives and treats effluent from one or more process to produce clarified water. This clarified water can be sent via a conduit 202 to one or more process. In certain instances, at least a portion of the clarified water is sent via a conduit 212 to the fermentation process. At least a portion of the clarified water may be sent by a conduit 232 to the gasification process 300 to be used as part of the gasification feed 301. At least a portion of the clarified water may be sent via a conduit 222 to the gasification process 300 to quench the syngas stream 302.

In certain instances, the wastewater treatment process 200 generates microbial biomass as part of the treatment process. At least a portion of this microbial biomass may be sent via a conduit 232 to the gasification process 300. Preferably, the gasification process 300 utilizes at least a portion of the microbial biomass generated by the wastewater treatment process 200 as part of the gasification feed 301.

The wastewater treatment process 200, as a by-product of treating microbial biomass, produces biogas. At least a portion of this biogas can be sent via a conduit 202 to the gasification process 300. In certain instances, at least a portion of the biogas is sent via a conduit 232 to the gasification process 300 to be used as part of the gasification feed 301. At least a portion of the biogas may be sent via a conduit 222 to the gasification process 300 to quench the syngas stream 302.

Preferably, the gasification process 300 receives one or more effluent from the fermentation process 100, product recovery process 400, and/or the wastewater treatment process 200 and produces a syngas stream 302. This syngas stream 302 is preferably suitable to use as a feedstock for the gas fermentation process 100.

To be suitable to use as a feedstock for the gas fermentation process 100, the syngas stream 302 should preferably have a desired composition. In particular instances, the syngas 302 produced by the gasification process 300 contains one or more constituent that needs to be removed and/or converted.

Typical constituents found in the syngas stream 302 that may need to be removed and/or converted include, but are not limited to, sulfur compounds, aromatic compounds, alkynes, alkenes, alkanes, olefins, nitrogen compounds, phosphorous-containing compounds, particulate matter, solids, oxygen, halogenated compounds, silicon-containing compounds, carbonyls, metals, alcohols, esters, ketones, peroxides, aldehydes, ethers, and tars. These constituents may be removed by one or more removal process.

Figure 2:
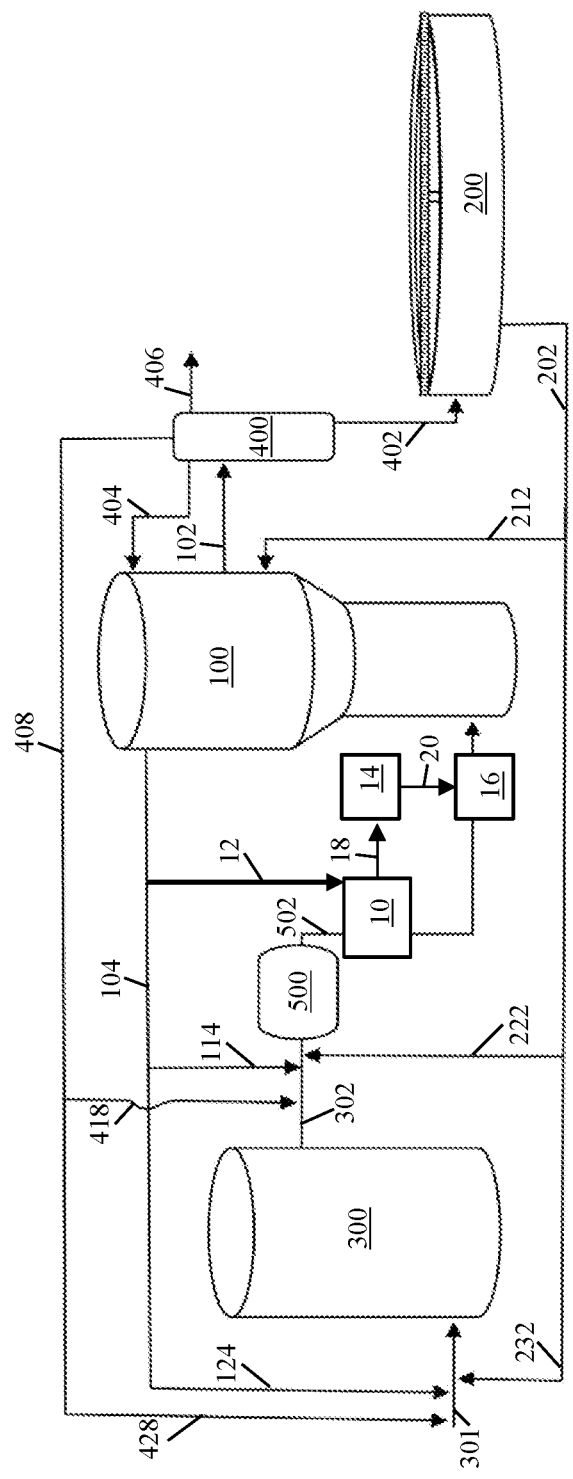
FIG. 2 shows the process integration scheme from FIG. 1, further comprising a removal process between the gasification process and the gas fermentation process, in accordance with one embodiment of the invention.

FIG. 2 shows the process integration scheme from FIG. 1, further comprising a removal process 500 between the gasification process 300 and the gas fermentation process 100, in accordance with one aspect of the invention, and in addition to the adsorption unit 10.

Preferably, the removal process 500 comprises one or more of the following modules: hydrolysis module, acid gas removal module, deoxygenation module, catalytic hydrogenation module, particulate removal module, chloride removal module, and hydrogen cyanide polishing module.

When incorporating a removal process 500, at least a portion of the syngas 302 from the gasification process 300 is sent to the removal process 500 to remove and/or convert at least a portion of at least one constituent found in the syngas stream 302. Preferably, the removal process 500 brings the constituents within allowable levels so as to produce a treated stream 502 suitable for fermentation by the fermentation process 100.

In various instances, the removal process 500 comprises two or more removal modules selected from the group comprising: hydrolysis module, acid gas removal module, deoxygenation module, catalytic hydrogenation module, particulate removal module, chloride removal module, and hydrogen cyanide polishing module. In certain instances, one or more of these removal modules are used to remove one or more constituent from the gas stream that may have adverse effects on downstream processes, for instance, the downstream fermentation process 100 and/or downstream removal modules within the removal process 500.

One or more constituent removed and/or converted by the removal process 500 may be introduced and/or concentrated through the gasification of microbial biomass. In certain instances, the removal process 500 removes ammonia ($NH_3$) and/or hydrogen cyanide (HCN). This ammonia and/or hydrogen cyanide may be introduced and/or concentrated when the microbial biomass is gasified by the gasification process 300. Ammonia and hydrogen cyanide can be produced from the nitrogen contained within the microbial biomass, which will undergo reaction in the gasification process 300 to become $N_2$, $NH_3$, and trace HCN.

Typically, the syngas stream being fed to the fermentation process 100 is gaseous. However, the syngas stream may also be provided in alternative forms. For example, the syngas stream may be dissolved in a liquid saturated with the syngas, which may then be fed to the fermentation process 100. By way of further example, the syngas may be adsorbed onto a solid support.

Preferably the fermentation process 100 utilizes C1-fixing microorganisms to ferment the syngas stream 302 and produce one or more product. The C1-fixing microorganism in the fermentation process 100 is typically a carboxydotrophic bacterium. In particular embodiments, the carboxydotrophic bacterium is selected from the group comprising *Moorella, Clostridium, Ruminococcus, Acetobacterium, Eubacterium, Butyribacterium, Oxobacter, Methanosarcina, Methanosarcina*, and *Desulfotomaculum*. In various embodiments, the carboxydotrophic bacterium is *Clostridium autoethanogenum*.

In certain instances, the one or more of the processes are integrated through by utilizing at least a portion of at least one effluent from one process as a heating source for at least one other process.

Figure 3:
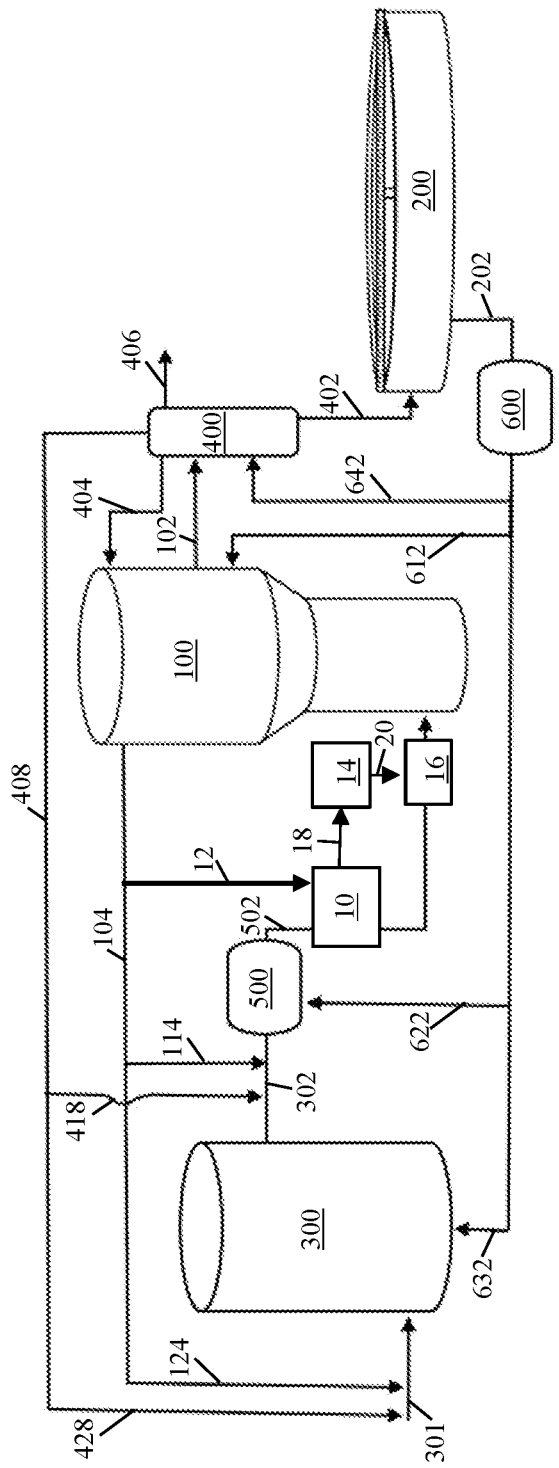
FIG. 3 shows the process integration scheme from FIG. 2, further comprising a removal process after the wastewater treatment process, in accordance with one embodiment of the invention.

FIG. 3 shows a process integration scheme depicting the integration of a gasification process 300, a gas fermentation process 100, a product recovery process 400, and a wastewater treatment process 200, in accordance with one aspect of the invention. In various instances, these processes are integrated by utilizing at least one effluent from at least one process as a heating source in at least one other process. In particular embodiments, the biogas generated by the wastewater treatment process 200 is utilized as a heating source for one or more process. Preferably, at least a portion of the biogas generated by the wastewater treatment process 200 is utilized as a heating source for the gasification process 300. In certain instances, the gasification process 300 utilizes at least a portion of the biogas generated by the wastewater treatment process 200 to melt at least a portion of a slag produced by the gasification process 300. In one or more embodiment, at least a portion of the biogas generated by the wastewater treatment process 200 is utilized as a heating source for the gas fermentation process 100. In one or more embodiment, at least a portion of the biogas generated by the wastewater treatment process 200 is utilized as a heating source for the product recovery process 400. In one or more embodiment, at least a portion of the biogas generated by the wastewater treatment process 200 is utilized as a heating source for the removal process 500.

In various instances, the biogas stream from the wastewater treatment process 200 is sent via a conduit 202 to at least one removal process 600 prior to being sent to one or more process. Preferably, the removal process 600 reduces the amount of at least one sulfur compound in the biogas stream.

When incorporating a removal process 600 following the wastewater treatment process 200, at least a portion of the biogas from the wastewater treatment process 200 is sent to the removal process 600 to remove and/or convert at least a portion of at least one constituent found in the biogas stream. Preferably, the removal process 600 brings the constituents within allowable levels so as to produce a treated stream 642, 612, 622, and/or 632 suitable to be used by the subsequent one or more process 400, 100, 500, and/or 300, respectively.

In particular embodiments, the tail-gas generated by the fermentation process 100 may also be used as a heating source for one or more process. For example, at least a portion of the tail-gas generated by the fermentation process 100 may be utilized as a heating source for the gasification process 300. In certain instances, the gasification process 300 utilizes at least a portion of the tail gas generated by the fermentation process 100 to melt at least a portion of a slag produced by the gasification process 300. In one or more embodiment, at least a portion of the tail gas generated by the fermentation process 100 is utilized as a heating source for the product recovery process 400. In various instances, the tail gas from the fermentation process 100 is sent to at least one removal process prior to being sent to one or more process.

In particular embodiments, unused syngas generated by the gasification process 300 is utilized as a heating source for one or more process. Preferably, at least a portion of the unused syngas generated by the gasification process 300 is utilized as a heating source for the gasification process 300. In certain instances, the gasification process 300 utilizes at least a portion of the unused syngas generated by the gasification process 300 to melt at least a portion of a slag produced by the gasification process 300. In one or more embodiment, at least a portion of the unused syngas generated by the gasification process 300 is utilized as a heating source for the product recovery process 400. In various instances, the unused syngas from the gasification process 300 is sent to at least one removal process prior to being sent to one or more process.

The fermentation process 100 is preferably capable of producing a variety of products. These products are preferably capable of being separated through use of a product recovery process 400. In various instances, at least a portion of at least one of the products produced by the fermentation process 100 may be used as a source for one or more process. In certain instances, at least a portion of the ethanol from the product recovery process 400 is utilized as a heating source for the gasification process 300. Preferably, the ethanol utilized as a heating source for one or more process is crude ethanol that does not meet the specification requirements for fuel-grade ethanol. In certain instances, the gasification process 300 utilizes at least a portion of the crude ethanol from the product recovery process 400 to melt at least a portion of a slag produced by the gasification process 300.

In certain instances, the fermentation process 100 produces fusel oil. This fusel oil may be recovered by the product recovery process 400 through any suitable means. For example, within the rectification column of a distillation setup. In at least one embodiment, at least a portion of the fusel oil from the product recovery process 400 is used as a heating source for one or more process. In certain instances, at least a portion of the fusel oil from the product recovery process 400 is utilized as a heating source for the gasification process 300. Preferably, the gasification process 300 utilizes at least a portion of the fusel oil from the product recovery process 400 to melt at least a portion of a slag produced by the gasification process 300.

Figure 4:
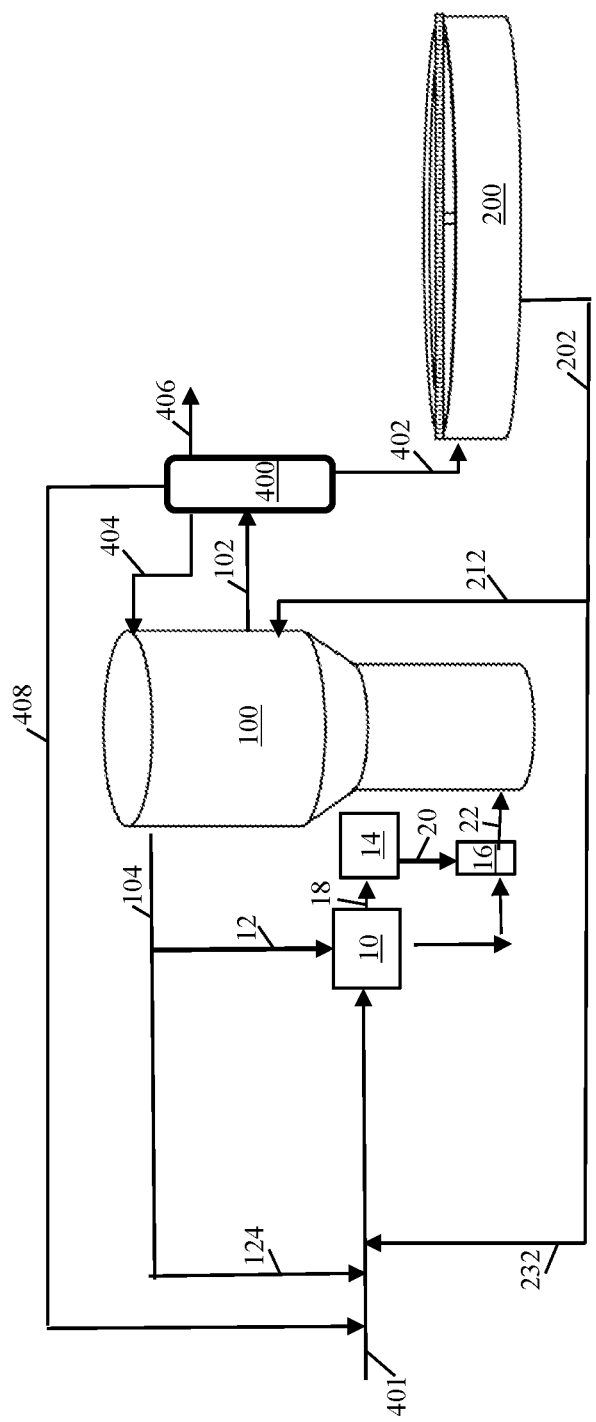
FIG. 4 shows process integration scheme depicting the integration of a gas fermentation process, a product recovery process, and a wastewater treatment process, where tail gas from the gas fermentation process is used as the purge gas for an adsorption unit on a feed stream and the enriched tail gas is conducted to a steam boiler to produce high pressure steam which is then used to power a compressor for the feed to a gas fermentation operation, in accordance with one embodiment of the invention.

FIG. 4 shows an embodiment using an industrial waste gas as the substrate or C1-carbon source without generating a syngas by gasification of a material. In various instances, the feed 401 is comprised of waste gas obtained as a by-product of an industrial process or from another source, such as automobile exhaust fumes, biogas or landfill gas or from electrolysis. The industrial process is selected from ferrous metal products manufacturing, such as a steel mill manufacturing, non-ferrous products manufacturing, petroleum refining, electric power production, carbon black production, paper and pulp manufacturing, ammonia production, methanol production, coke manufacturing, or any combination thereof. Optionally, the feed 401 may also comprise at least one effluent from the fermentation process 100, at least one effluent from the product recovery process 400, and at least one effluent from the wastewater treatment process 200.

The fermentation process 100 utilizes the feed stream as a carbon source for producing one or more product, which may be at least partially contained in one or more effluent stream 102, 104. In various instances, the effluent from the fermentation process 100 is fermentation broth. However, certain components of the feed are to be removed in an adsorption unit 10 before the treated feed is passed via line 22 and fermented in the fermentation process 100. Components removed include at least one of a hydrocarbon, an oxygenate, a sulfur compound, and or nitrogen compound. Typical components that may be found in the feed 401 that may need to be removed by the adsorption unit include, but are not limited to, sulfur compounds, aromatic compounds, alkynes, alkenes, alkanes, olefins, nitrogen compounds, phosphorous-containing compounds, particulate matter, solids, oxygen, halogenated compounds, silicon-containing compounds, carbonyls, metals, alcohols, esters, ketones, peroxides, aldehydes, ethers, and tars.

The component(s) are adsorbed onto the adsorbent of the adsorption unit 10. The adsorption unit may be a temperature swing adsorption system, a pressure swing adsorption system, a swing bed system, a moving bed system, or a fixed bed system. Over time the adsorbent may reach capacity and need regeneration. A desorbent and or purge gas is helpful to regenerate the adsorbent. At least a portion of tail gas 104 of fermentation process 100 may be used as the desorbent or purge 12 for adsorption unit 10. The tail gas used as desorbent or purge 12 for adsorption unit 10 becomes enriched in components desorbed from the adsorbent including the at least one hydrocarbon, oxygenate, sulfur compound and or nitrogen compound to form an enriched tail gas 18 that has a higher calorific value than tail gas desorbent 12. In this embodiment, enriched tail gas 18 is conducted to steam boiler 14 to generate high pressure steam 20. High pressure steam 20 is provided to system 16 which generates power from the high-pressure steam and powers a compressor which compresses the feed before it is introduced to the gas fermentation process 100 via line 22.

An effluent from the fermentation process 100 is tail gas generated by the fermentation process 100. A portion of the tail gas is conducted in line 104, and 12 for use as a desorbent and or purge gas for adsorption unit 10. In an optional embodiment, at least a portion of the tail gas may be sent by a conduit 124 to combine with feed 401.

One or more products produced by the fermentation process 100 are removed and/or separated from the fermentation broth by a product recovery process 400 as discussed above. Similarly, in at least one embodiment, an effluent from the fermentation process 100 is fermentation broth, and at least a portion of the fermentation broth is sent via a conduit 102 to the product recovery process 400, as discussed above.

Figure 5:
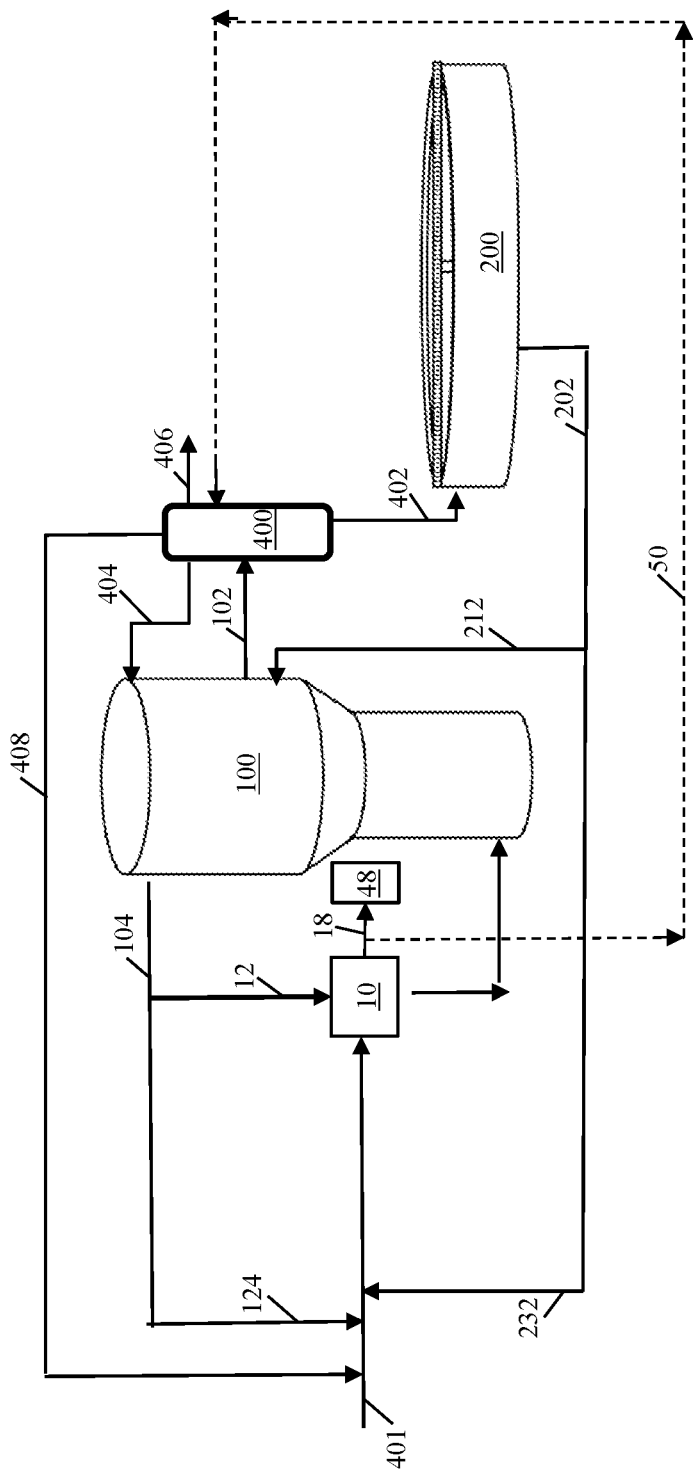
FIG. 5 shows an embodiment using an industrial waste gas as the substrate or C1-carbon source without generating a syngas by gasification of a material wherein the enriched tail gas in line is directed to a power generation unit.

FIG. 5 shows an embodiment using an industrial waste gas as the substrate or C1-carbon source without generating a syngas by gasification of a material wherein the enriched tail gas in line 18 is directed to a power generation unit 48. FIG. 5 also shows an alternative embodiment where the enriched tail gas in line 18 is directed to the process recovery process and unit 400 via line 50 to, for example, dry the product.

Figure 6:
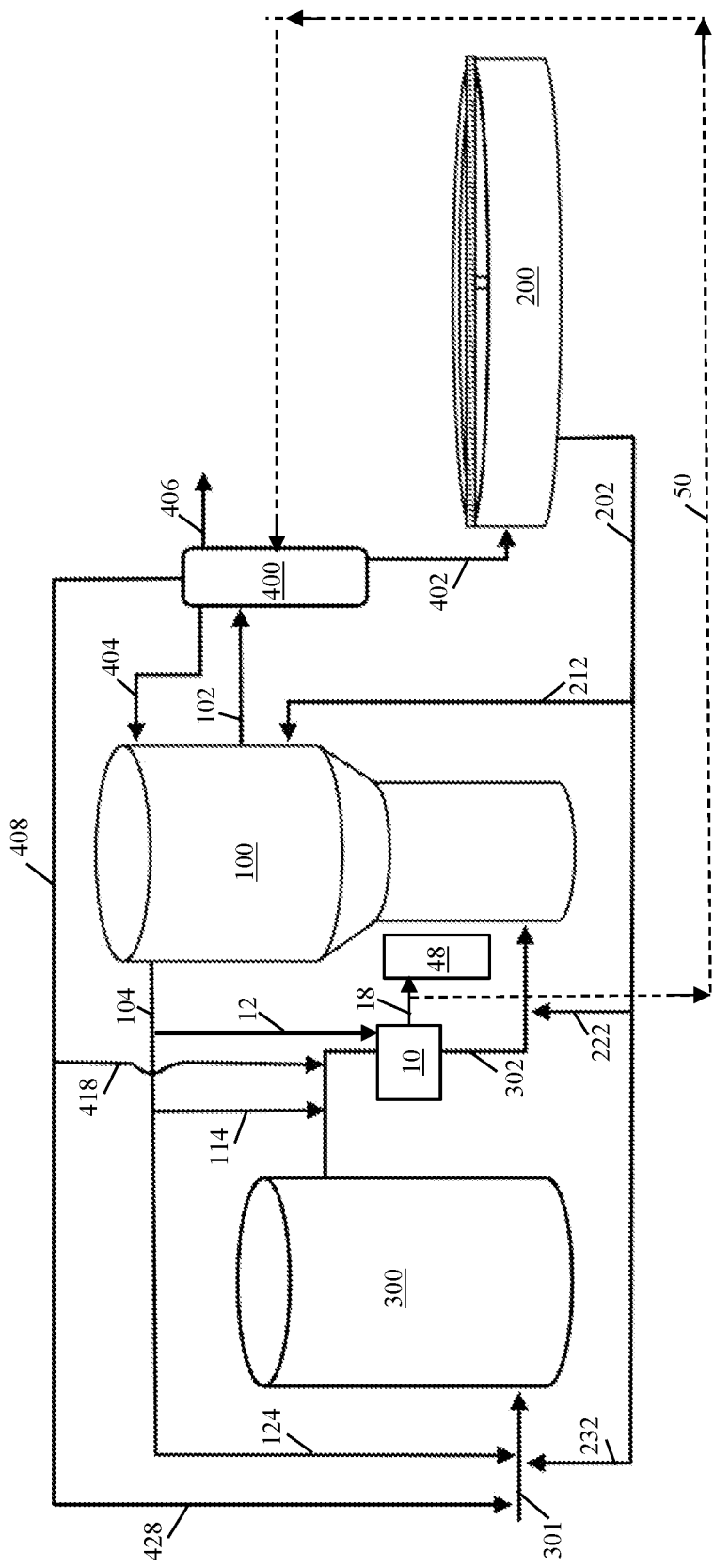
FIG. 6 shows an embodiment using a gasifier to generate syngas as the substrate or C1-carbon source wherein the enriched tail gas is directed to a power generation unit.

FIG. 6 shows an embodiment using a gasifier 300 to generate syngas as the substrate or C1-carbon source wherein the enriched tail gas in line 18 is directed to a power generation unit. FIG. 6 also shows an alternative embodiment where the enriched tail gas is directed to a product recovery process and unit 400 to, for example, dry the product.

In instances where the fermentation broth is processed by the product recovery process 400, at least a portion of the microbial biomass depleted water, produced through the removal of microbial biomass from the fermentation broth, may be returned to the fermentation process 100 via a conduit 404 and/or sent via a conduit 408 to be used as part of the feed 401. Additionally, at least a portion of the effluent from the product recovery process 400 may be sent via a conduit 402 to the wastewater treatment process 200. Preferably, the effluent from the product recovery process 400 comprises reduced amounts of product and/or microbial biomass.

All references, including publications, patent applications, and patents, cited herein are hereby incorporated by reference to the same extent as if each reference were individually and specifically indicated to be incorporated by reference and were set forth in its entirety herein. The reference to any prior art in this specification is not, and should not be taken as, an acknowledgment that that prior art forms part of the common general knowledge in the field of endeavor in any country.

The use of the terms "a" and "an" and "the" and similar referents in the context of describing the invention (especially in the context of the following claims) are to be construed to cover both the singular and the plural unless otherwise indicated herein or clearly contradicted by context. The terms "comprising," "having," "including," and "containing" are to be construed as open-ended terms (e.g., meaning "including, but not limited to") unless otherwise noted. The term "consisting essentially of" limits the scope of a composition, process, or method to the specified materials or steps, or to those that do not materially affect the basic and novel characteristics of the composition, process, or method. The use of the alternative (e.g., "or") should be understood to mean either one, both, or any combination thereof of the alternatives. As used herein, the term "about" means±20% of the indicated range, value, or structure, unless otherwise indicated.

Recitation of ranges of values herein is merely intended to serve as a shorthand method of referring individually to each separate value falling within the range, unless otherwise indicated herein, and each separate value is incorporated into the specification as if it were individually recited herein. For example, any concentration range, percentage range, ratio range, integer range, size range, or thickness range is to be understood to include the value of any integer within the recited range and, when appropriate, fractions thereof (such as one tenth and one hundredth of an integer), unless otherwise indicated.

All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:
1. A method comprising:
   a. gasifying a gasification feedstock to produce syngas comprising at least carbon monoxide, hydrogen, water, and tars;
   b. cooling the syngas to separate water and at least one tar by condensation and provide a remainder of the syngas depleted in water and at least one tar;
   c. disposing of the at least one tar by:
      i. combusting the at least one tar using a flame produced by the combustion of fuel gas, natural gas, syngas, tail gas from a gas fermentation process, or any combination thereof; or
      ii. passing the at least one tar to a wastewater treatment process;
   d. treating the remainder of the syngas by adsorbing on an adsorbent a component comprising at least one of a hydrocarbon, an oxygenate, a sulfur compound, a nitrogen compound, or any combination thereof and generating a treated stream;
   e. fermenting at least a portion of the treated stream in a bioreactor using a microorganism to generate an effluent comprising at least one product and a tail gas stream comprising at least carbon dioxide;
   f. regenerating the adsorbent by at least partially desorbing the component using at least a portion of the tail gas stream to provide an enriched tail gas stream comprising the carbon dioxide and the desorbed component; and
g. utilizing the enriched tail gas stream in at least one of:
 i. combusting in a steam boiler to produce steam;
 ii. generating power;
 iii. recycling to the gasification process; or
 iv. passing to a product recovery zone.

2. The method of claim 1 wherein the tail gas further comprises methane, carbon monoxide, and hydrogen.

3. The method of claim 1 wherein the microorganism is one or more C1-fixing microorganisms.

4. The method of claim 3 wherein C1-fixing microorganism is selected from *Moorella, Clostridium, Ruminococcus, Acetobacterium, Eubacterium, Butyribacterium, Oxobacter, Methanosarcina*, and *Desulfotomaculum*.

5. The method of claim 1 wherein the steam is high pressure steam.

6. The method of claim 1 further comprising employing the steam for distillation of fermentation products, operation of an adsorption chiller, steam driven compression, evaporation of waste water, drying of biomass, steam in place operations, clean in place operations, drying of feedstock, steam driven feedstock conveyors, heating of buildings, generation of power, and generating power to power a compressor of the fermentation process.

7. The method of claim 1 wherein the industrial waste gas is from processes selected from ferrous metal products manufacturing, non-ferrous products manufacturing, petroleum refining, electric power production, carbon black production, paper and pulp manufacturing, ammonia production, methanol production, coke manufacturing, and any combination thereof, and or the syngas stream is from the gasification of coal, gasification of refinery residues, gasification of biomass, gasification of lignocellulosic material, black liquor gasification, gasification of municipal solid waste, gasification of industrial solid waste, gasification of sewerage, gasification of sludge from wastewater treatment, reforming of natural gas, reforming of biogas, reforming of landfill gas or any combination thereof.

8. The process of claim 1 wherein the generating power is cogeneration or direct generation.

9. The process of claim 1 wherein the tail gas stream, as compared to the syngas stream from a gasification process or the industrial waste gas, is
 a. enriched in $N_2$;
 b. enriched in $CO_2$;
 c. depleted in impurities; or
 d. any combination of (a) (b) or (c).

10. The process of claim 9 wherein the desorbing the component using at least a portion of the tail gas stream is improved as compared to desorbing the component using a syngas stream.

* * * * *